US006734338B1

(12) United States Patent
Readhead et al.

(10) Patent No.: US 6,734,338 B1
(45) Date of Patent: *May 11, 2004

(54) TRANSFECTION, STORAGE AND TRANSFER OF MALE GERM CELLS FOR GENERATION OF TRANSGENIC SPECIES AND GENETIC THERAPIES

(75) Inventors: Carol W. Readhead, Pasadena, CA (US); Robert Winston, London (GB)

(73) Assignees: Cedars-Sinai Medical Center, Los Angeles, CA (US); IMPEL, Imperial College of Science, Technology and Medicine, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/311,599

(22) Filed: May 13, 1999

Related U.S. Application Data

(63) Continuation-in-part of application No. 09/292,723, filed on Apr. 15, 1999, which is a continuation-in-part of application No. 09/191,920, filed on Nov. 13, 1998, now Pat. No. 6,316,692

(60) Provisional application No. 60/065,825, filed on Nov. 14, 1997.

(51) Int. Cl.[7] .......................... C12P 21/00; C12H 15/00
(52) U.S. Cl. .............................. 800/23; 800/21; 800/4
(58) Field of Search ............................. 800/21, 22, 24, 800/25, 13, 14, 18; 435/455

(56) References Cited

U.S. PATENT DOCUMENTS

| | | |
|---|---|---|
| 4,663,281 A | 5/1987 | Gillies et al. |
| 4,762,701 A | 8/1988 | Horan et al. |
| 4,870,009 A | 9/1989 | Evans et al. |
| 4,959,313 A | 9/1990 | Taketo |
| 4,978,332 A | 12/1990 | Luck et al. |
| 5,175,384 A | 12/1992 | Krimpenfort et al. |
| 5,206,143 A | 4/1993 | Horan et al. |
| 5,358,711 A | 10/1994 | May et al. |
| 5,375,606 A | 12/1994 | Slezak et al. |
| 5,422,266 A | 6/1995 | Cormier et al. |
| 5,430,057 A | 7/1995 | Andersson et al. |
| 5,434,340 A | 7/1995 | Krimpenfort et al. |
| 5,491,084 A | 2/1996 | Chalfie et al. |
| 5,521,291 A | 5/1996 | Curiel et al. |
| 5,532,143 A | 7/1996 | Grosveld et al. |
| 5,543,291 A | 8/1996 | Keyomarsi et al. |
| 5,547,932 A | 8/1996 | Curiel et al. |
| 5,556,954 A | 9/1996 | Burn et al. |
| 5,559,148 A | 9/1996 | Andersson et al. |
| 5,591,625 A | 1/1997 | Gerson et al. |
| 5,591,669 A | 1/1997 | Krimpenfort et al. |
| 5,610,053 A | 3/1997 | Chung et al. |
| 5,625,048 A | 4/1997 | Tsien et al. |
| 5,639,618 A | 6/1997 | Gay |
| 5,643,741 A | 7/1997 | Tsukamoto et al. |
| 5,650,135 A | 7/1997 | Contag et al. |
| 5,665,557 A | 9/1997 | Murray et al. |
| 5,670,372 A | 9/1997 | Hogan |
| 5,750,376 A | 5/1998 | Weiss et al. |
| 5,767,258 A | 6/1998 | Sidransky |
| 5,777,079 A | 7/1998 | Tsien et al. |
| 5,821,234 A | 10/1998 | Dzau |
| 5,840,478 A | 11/1998 | Patterson et al. |

FOREIGN PATENT DOCUMENTS

| | | |
|---|---|---|
| EP | 0 867 114 A1 | 9/1998 |
| WO | WO 90/08192 | 7/1990 |
| WO | WO 92/03459 | 3/1992 |
| WO | WO 93/11228 | 6/1993 |
| WO | WO 95/02041 | 1/1995 |

OTHER PUBLICATIONS

Avarbock, Mary R., et al., Reconstitution of spermatogenesis from frozen spermatogonial stem cells, *Nature Medicine*, vol. 2, No. 6, pp. 693–696, (Jun., 1996).

Baranov, V. S., et al., *The possibility of the incorporation of macromolecules, including exogenous DNA, into the germ cells of male mice. The liposome method and Ca–P coprecipitation method*, *Tsitol Genet*, vol. 24, No. 2, pp. 52–55 (Mar. 1990). Abstract Only.

Birnstiel, Max L. et al., *Dangerous Liaisons: Spermatozoa as Natural Vectors for Foreign DNA?*, Cell, vol. 57, pp. 701–702, (1989).

Blanchard, K.. T. et al., *Adenovirus–mediated gene transfer to rat testis in vivo*, Biol Reprod (Feb. 1997); 56(2):495–500.

Brinster, Ralph L., et al., *No Simple Solution for Making Transgenic Mice*, Cell, vol. 59, pp. 239–241, Oct. 20, 1989.

Brinster, Ralph L. et al., Avarbock, *Germline transmission of donor haplotype following spermatogonial transplantation*, Proc. Natl. Acad. Sci. USA, vol. 91, pp. 22303–22307, (Nov. 1994) Developmental Biology.

(List continued on next page.)

*Primary Examiner*—Deborah J. Reynolds
*Assistant Examiner*—Joseph Woitach
(74) *Attorney, Agent, or Firm*—Sidley Austin Brown & Wood LLP

(57) ABSTRACT

A composition for in vitro and in vivo transfection of vertebrate male germ cells comprises a nucleic acid or transgene, and a gene delivery system, and optionally a protective internalizing agent, such as an endosomal lytic agent, a virus or a viral component, which is internalized by cells along with the transgene and which enhances gene transfer through the cytoplasm to the nucleus of the male germ cell. A method of genetically altering a vertebrate male germ cell in vivo employs a lentiviral-derived vector. A method of substantially depopulating a vertebrate testis employs a combination of a dose of an alkylating agent, such as busulfan, chlorambucil, cyclophosphamide, melphalan, or ethyl ethanesulfonic acid, and a dose of gamma radiation. A pharmaceutical preparation and a transfer kit utilize the composition. A method for introducing a polynucleotide into vertebrate male germ cells comprises the administration of the composition to a vertebrate. A method for isolating or selecting transfected cells utilizes a reporter gene, and a method for administering transfected male germ cells utilizes male germ cells which have been transfected in vitro.

45 Claims, 3 Drawing Sheets

OTHER PUBLICATIONS

Brinster, Ralph L. et al., *Spermatogenesis following male germ–cell transplantation*, Proc. Natl. Acad. Sci. USA, Vo. 91, pp. 11298–11302, (Nov. 1994), Developmental Biology.

Chen, Shu–Hsia et al., *Gene therapy for brain tumors: Regression of experimental gliomas by adenovirus–mediated gene transfer in vivo*, Proc. Natl. Acad. Sci, USA, vol. 91, pp. 3054–3057, Apr. 1994.

Chung, J. H. et al., *A 5' element of the chicken beta–globin domain serves as an insulator in human erythroid cells and protects against position effect in Drosophila*, Cell, 74(3):505–14, Aug. 13, 1993, Abstract Only.

Chung, J. H. et al., *Characterization of the chicken beta–globin insulator*, Proc. Natl. Acad. Sci. USA. 94(2):575–80, Jan. 21, 1997, Abstract Only.

Clouthier, D. E. et al., *Rat spermatogenesis in mouse testis*, Nature, 381(6581): 418–421 (May 30, 1996).

Curiel D. T., et al. *Adenovirus enhancement of transferrin–polylysine–mediated gene delivery*, Proc. Natl. Acad. Sci–USA, 88:8850–54(Oct. 1991).

Desdouets, C. et al, *Cyclin A: function and expression during cell proliferation*, Prog Cell Cycles Res, 1:115–23, 1995, Abstract Only.

Graberek & Gergely, *Zero–length cross–linking procedure with the use of active esters*, Analyt. Biochem 185: 131–135 (1990).

Hagstrom, K., et al., *Fab–7 functions as a chromatin domain boundary to ensure proper segment specification by the Drosophila bithorax complex*, Genes Dev, 10(24):3202–15, Dec. 15, 1996, Abstract Only.

Horiguchi–Yamada, J., et al., *Changes of G1 cyclins, edk2, and cyclin A during the differentiation of HL60 cells induced by TPA*, Mol Cell Biochem, 132(1):31–7, Mar. 16, 1994, Abstract Only.

Hovatta, Outi, et al., *Cryopreservation of human ovarian tissue using dimethysulphoxide and propanediol–sucrose as cryoprotectants*, Human Reproduction, vol. 11, No. 6, pp. 1268–1272, (1996).

Hovatta, Outi, et al., *Pregnancy resulting from intracytoplasmic injection of spermatozoa from a frozen–thawed testicular biopsy specimen*, Human Reproduction, vol. 11, No. 11, pp. 2472–2473, (1996).

Jiang, F–X et al., *Male germ cell transplantation in rats: apparent syunchronization of spermatogenesis between host and donor seminiferous, epithelia*, International Journal of Andrology, vol. 18, pp. 326–330 (1995).

Jiang, Fang–Xu et al., *Different fate of primordial germ cells and gonocytes following transplantation*, APMIS, vol. 106, p. 58–63, (1998).

Johnson L, et al., *Heterotoic transplantation as a model to study the regulation of spermatogenesis; some histomorphological considerations about sperm decline in man; Contracept Fertil Sex* 1997 vol. 25(7–8), pp. 549–555, (1997).

Jones and Shenk, *An adenovirus type 5 early gene function regulates expression of other early viral genes*, Proc. Natl. Acad. Sci. USA, 76:(8)3665–3669 (1979).

Kang, M. J. et al., *Cyclins and cyclin dependent kinases during cardiac development*, Mol Cells, 7(3):360–6, (Jun. 30, 1997) Abstract Only.

Kim, Jin–Hoi et al., *Development of a Positive method for Male stem Cell–Mediated Gene Transfer in Mouse and Pig*, Molecular Reporduction and Development, vol. 46, No. 4, pp. 515–526, (1997).

Kim, V. Narry et al., *Minimal requirement for a Lentivirus Vector Based on Human Immunodeficiency Virus Type 1*, Journal of Virology, pp. 811–816, (Jan. 1998).

Langer, Robert S. et al., *Tissue Engineering: The obstacles to building new organs from cells and synthetic polymers are daunting but surmountable The Challenges Ahead*, Scientific American, pp. 86–89, Apr. 1999.

Lavitrano, Mariauisa et al., *Sperm Cells as Vectors for Introducing foreign DNA Into Eggs: Genetic Transformation of Mice*, Cell, vol. 57, pp. 717–723, (Jun. 2, 1989).

Mittereder et al., *Evaluation of the concentration and bioactivity of adenovirus vectors for gene therapy*, J. Virology, 70: 7498–7509 (1996).

Müller, C. et al., *Cell cycle regulated transcription of the promoter of the human cyclin A1 gene*, Blood, Journal of the American Society of Hematology, vol. 90, No. 10, Suppl 1 (Part 1 of 2) Nov. 15, 1997 Abstract 1404.

Müller, C. et al., *SP1 Family Members Regulate Expression of the Tissue Specific Human Cyclin A1 Gene*, Blood Journal of the American society of Hematology, Americ. Soc. Of Hemat.40th Annual Meeting, Dec. 4–8, 1998 Abstract 1534.

Müller, Carsten et al., *Cloning of the cyclin A1 Genomic Structure and Characterization of the Promoter Region*, The Journal of Biological Chemistry vol. 276, No. 16, pp. 11220–11228, Apr. 16, 1998.

Muramatsu T. et al., *Foreign gene expression in the mouse testis by localized in vivo gene transfer*, Biochem Biophys Res commun, 7;233(1):45–49 (Apr. 1997).

Nagano, M, et al., *Spermatogonial transplantation and reconstitution of donor cell spermatogenesis in recipient mice*, APMIS, 106, pp. 47–55, (1998).

Americ. Soc. Of Hemat.40th Annual Meeting, Dec. 4–8, 1998 Abstract 1534.

Naito M, et al., *Production of germline chimeric chickens, with high transmission rate of donor–derived gametes, produced by transfer of primordial germ cells*, Molecular Reprod Dev., 39(2):153–161(Oct. 1994).

Naito M, et al., *Donor primordial germ cell–derived offspring from recipient germline chimaeric chickens: absence of long–term immune rejection and effects on sex ratios*, Br Poult Sci, 39(1):20–23 (Mar. 1998).

Naldini, Luigi et al., *In Vivo Gene Delivery and Stable Transduction of Nondividing Cells by a Lentiviral Vector*, Science, vol. 272, pp. 263–269 Apr. 12, 1996.

Ogawa, Takehiko et al., *Transplantation of testis germinal cells into mouse seminiferous tubules*, Int. J. Dev. Biol., 41:222–122 (1997).

Ono T. et al., *Transfer of male or female primordial germ cells of quail into chick embryonic gonads*, Exp Anim, 45(4):347–352 (Oct. 1996).

Paterlini, P. et al., *Cylin A expression in human hematological malignancies: a new marker of cell proliferation*, Cancer Res, 53(2):235–8, (Jan. 15, 1993) Abstract Only.

Pedersen, Roger A., *Cells for Medicine,Embryonic Stem Cells for Medicine*, Scientific American, pp. 68–73 (Apr. 1999).

Perez–Cruet, M. J., et al., *Adenovirus–Mediated Gene Therapy of Experimental gliomas*, Journal of Neuroscience Research, vol. 39, pp 506–511(1994). meiotic cell cycles, Dev. Biol., 10:173(1):69–78, (Jan. 10, 1996).

Pikaart, Michael J., *Loss of transcriptional activity of a transgene is accompanied by DNA methylation and histone deacetylation and is prevented by insulators*, Genes & Development, 12:2852–2862, (1998).

Ravnik, S. E. et al., *The developmentally restricted pattern of expression in the male germ line of a murine cylin A, cyclin A2, suggests roles in both mitotic and meiotic cell cycles*, Dev. Biol., 10:173(1):69–78, (Jan. 10, 1996). Abstract Only.

Ravnik, S. E. et al., *Regulation of meiosis during mammalian spermatogenesis: the A–type cyclins and their associated cyclin–dependent kinases are differentially expressed in the germ–cell lineage*, Dev Bio, 207(2):408–18 (Mar. 15, 1999). Abstract Only.

Russell, L.D. et al., *Ultrastructural observations of spermatogenesis in mice resulting from transplantatin of mouse spermatogonia*, J. Androl., 17(6):603–614 (Nov. 1996).

Schmidt, Jerzy A. et al., *Control of Erythroid differentation. Possible Role of the Transferrin cycle*, Cell, vol. 46, 41–51 (Jul. 4, 1986).

Schiedner, Gudrun, *Genomic DNA transfer with a high–capacity adenovirus vector results in improved in vivo gene expression and decreased toxicity*, Nature Genetics, vol. 18, pp. 180–183 (Feb. 1998).

Sweeney, Claire et al., *A distinct cyclin A is expressed in germ cells in the mouse*, Development, vol. 122, pp. 53–64 (1996).

Wagner, Ernst, *Transferrin–polycation conjugates as carriers for DNA uptake into cells*, Proc. Natl. Acad. Sci. USA, Vol 87, pp. 3430–3414 (May 1990).

Wolffe, A. P., *Packaging principle: how DNA methylation and histone acetylation control the trancriptional activity of chromatin*, J. Exp Zool, 282(1–2):239–44 (Sep.–Oct. 1998). Abstract Only.

Yang, Rong et al., *Characterization of a Second Human Cylin A That is Highly Expressed in Testis and in Several Leukemic Cell Lines*, Cancer Research, 57, pp. 913–920 (Mar. 1, 1997).

PCT International Search Report.

XP–002099974, J09220039, "Introducing Extraneous Gene Sperm Ovum Produce Transgenic Animal Comprise Introducing Extraneous Gene Liposome Complex Through Testicular Ovary Artery Sperm Testicular Ovum Ovary", Abstract Only.

Bucci, L. R. et al., *Effects of busulfan on murine spermatogenesis: cytotoxicity, sterility, sperm abnormalities, and dominant lethal mutations*, Research, vol. 176, pp. 259–268, (1987).

Kormano, M. et al., *In vitro contractility of rat seminiferous tubules following 400 R whole–body X–irradiation*, Strahlentherapie vol. 144, No. 6, pp. 713–718 (1972).

Oakberg, E. F., *Effects of radiation on the testis*, Handbook of Physiology, Endocrinology V, pp. 233–243 (date unknown).

Pont, Jorg et al., *Fertility after chemotherapy for testicular germ cell cancer*, Fertility and Sterility, vol. 68, No. 1, pp. 1–5, (Jul. 1997).

Boujrad, N. et al., *Evolution of somatic and germ cell populations after busulfan treatment in utero or neonatal cryptorchidism in the rat*, Andrologia, 27(4):223–8 (Jul.–Aug. 1995). Abstract Only.

Hasegawa, M., *Resistance of differentiating sprematogonia to radiation–induced apoptosis and loss in p53–deficient mice*, Radiat Res, 149(3):263:70, (Mar. 1998). Abstract Only.

Hopkinson, C. R., *The effect of local testicular irradiation on testicular histology and plasma hormone levels in the male rat*, Acta Endocrinol (Copenh), 87(2):413–23 (Feb. 1998). Abstract Only.

Jiang, F. X., Anat Embryol, *Behaviour of spermatogonia following recovery from busulfan treatment in the rat*, 198(1):53–61 (Jul. 1998). Abstract Only.

Kamtchouing, P., *Effect of continuous low–dose gamma–irradiation on rat Sertoli cell function*, Reprod Nutr Dev, 28(4B):1009–17 (1988). Abstract Only.

Kamtchouing, P., *Changes in androgen binding protein (ABP) production following continuous low dose gamma irradiation (IR) of adult rat*, Steroid, 52((4):349–50, (Oct. 1988). Abstract Only.

Kangasniemi, M., *Cellular regulation of basal and FSH–stimulated cyclic AMP production in irradiated rat testes*, 227(1):32–6 (May 1990). Abstract Only.

Kasuga, F., *The endocrine function of rat gonads with reduced number of germ cells following busulphan treatment*, Endocrinol Jpn, 33(1):105–15 (Feb. 1986). Abstract Only.

Linder, R. E., *Endpoints of spermatotoxicity in the rat after short duration exposures to fourteen reproductive toxicants*, Reprod Toxicol, 6(6):491–505 (1992). Abstract Only.

Pineau, C., *Assessment of testicular function after acute and chronic irradiation: further evidence for an influence of late spermatids on Sertoli cell function in the adult rat*, Endocrinology, 124(6):2720–8 (Jun. 1989). Abstract Only.

Pinon–Lataillade, G. et al., *Continuous gamma–irradiation of rates: dose–rate effect on loss and recovery of spermatogenesis*, Strahlentherapie, 161(7):421–6, (Jul. 1985). Abstract Only.

Pinon–Lataillade, G. et al., *Endocrinological and histological changes induced by continuous low dose gamma–irradiation of the rat testis*, Acta Endocrinol (Copenh), 109(4):558–62 (Aug. 1985). Abstract Only.

Pinon–Lataillade, G. et al., *Influence of germ cells upon Sertoli cells during continuous low–dose rate gamma–irradiation of adult rats*, Mol Cell Endocrinol, 58(1):51–63, (Jul. 1988). Abstract Only.

Pinon–Lataillade, G., *Effect of an acute exposure of rat trestes to gamma rays on germ cells and on Sertoli and Leydig cell functions*, Reprod Nutr Dev 31(6):617–29. (1991) Abstract Only.

Russell, L. D. et al., *Ultrastructural observations of spermatogenesis following transplantation of rat testis cells into mouse seminiferous tubules*, J. Androl 17(6):615–27. (Nov.–Dec. 1996). Abstract Only.

Announcement re Bulsulfan (Myleran) Facts and Comparisons, pp. 1–5 (Aug. 1997).

Ogawa, Takehiko et al., *Xenogeneic Spermatogenesis Following Transplantation of Hamster Germ Cells to Mouse Testes*, Biology of Reproduction, vol. 60, pp. 515–521 (1999).

TRANSFECTION, STORAGE AND TRANSFER OF MALE GERM CELLS FOR GENERATION OF TRANSGENIC SPECIES AND GENETIC THERAPIES

This application is a continuation-in-part of U.S. Ser. No. 09/292,723, filed Apr. 15, 1999, which is a continuation-in-part of U.S. patent application Ser. No. 09/191,920, filed Nov. 13, 1998 now U.S. Pat. No 6,316,692, which claims the benefit of U.S. Provisional Application No. 60/065825, filed on Nov. 14, 1997.

The U.S. Government has a paid-up license in this invention and the right in limited circumstances to require the patent owner to license others on reasonable terms as provided for by the terms on NIH Grant No. RO1 RR12406.

BACKGROUND OF THE INVENTION

Throughout this application various publications are referenced within parentheses. The disclosures of these publications in their entireties are hereby incorporated by reference in this application in order to more fully describe the state of the art to which this invention pertains.

1. The Field of the Invention

This invention relates to the medical arts, particularly to the field of transgenics and gene therapy The invention is particularly directed to in vitro and in vivo methods for transfecting male germ cells and support cells (i.e., Leydig and Sertoli cells), which methods incorporate a method of depopulating a vertebrate testis of male germ cells.

2. Discussion of the Related Art

The field of transgenics was initially developed to understand the action of a single gene in the context of the whole animal and phenomena of gene activation, expression, and interaction. This technology has been used to produce models for various diseases in humans and other animals. Transgenic technology is amongst the most powerful tools available for the study of genetics, and the understanding of genetic mechanisms and function It is also used to study the relationship between genes and diseases About 5,000 diseases are caused by a single genetic defect. More commonly, other diseases are the result of complex interactions between one or more genes and environmental agents, such as viruses or carcinogens. The understanding of such interactions is of prime importance for the development of therapies, such as gene therapy and drug therapies, and also treatments such as organ transplantation Such treatments compensate for functional deficiencies and/or may eliminate undesirable functions expressed in an organism. Transgenesis has also been used for the improvement of livestock, and for the large scale production of biologically active pharmaceuticals.

Historically, transgenic animals have been produced almost exclusively by micro injection of the fertilized egg. The pronuclei of fertilized eggs are micro injected in vitro with foreign, i.e. xenogeneic or allogeneic DNA or hybrid DNA molecules. The micro injected fertilized eggs are then transferred to the genital tract of a pseudopregnant female. (E.g., P. J. A. Krimpenfort et al., Transgenic mice depleted in mature T-cells and methods for making transgenic mice, U.S. Pat. Nos. 5,175,384 and 5,434,340; P. J. A. Krimpenfort et al., Transgenic mice depleted in mature lymphocytic cell-type, U.S. Pat. No. 5,591,669).

The generation of transgenic animals by this technique is generally reproducible, and for this reason little has been done to improve on it. This technique, however, requires large numbers of fertilized eggs. This is partly because there is a high rate of egg loss due to lysis during micro injection. Moreover manipulated embryos are less likely to implant and survive in utero. These factors contribute to the technique's extremely low efficiency. For example, 300–500 fertilized eggs may need to be micro injected to produce perhaps three transgenic animals. Partly because of the need to micro inject large numbers of embryos, transgenic technology has largely been exploited in mice because of their high fecundity. Whilst small animals such as mice have proved to be suitable models for certain diseases, their value in this respect is limited. Larger animals would be much more suitable to study the effects and treatment of most human diseases because of their greater similarity to humans in many aspects, and also the size of their organs. Now that transgenic animals with the potential for human xenotransplantation are being developed, larger animals, of a size comparable to man will be required. Transgenic technology will allow that such donor animals will be immunocompatible with the human recipient. Historical transgenic techniques, however, require that there be an ample supply of fertilized female germ cells or eggs. Most large mammals, such as primates, cows, horses and pigs produce only 10–20 or less eggs per animal per cycle even after hormonal stimulation. Consequently, generating large animals with these techniques is prohibitively expensive.

This invention relies on the fact that vast numbers of male germ cells are more readily available. Most male mammals generally produce at least $10^8$ spermatozoa (male germ cells) in each ejaculate. This is in contrast to only 10–20 eggs in a mouse even after treatment with superovulatory drugs. A similar situation is true for ovulation in nearly all larger animals. For this reason alone, male germ cells will be a better target for introducing foreign DNA into the germ line, leading to the generation of transgenic animals with increased efficiency and after simple, natural mating.

Spermatogenesis is the process by which a diploid spermatogonial stem cell provides daughter cells which undergo dramatic and distinct morphological changes to become self-propelling haploid cells (male gametes) capable, when fully mature, of fertilizing an ovum.

Primordial germ cells are first seen in the endodermal yolk sac epithelium at E8 and are thought to arise from the embryonic ectoderm (A. McLaren and Buehr, Cell Diff. Dev. 31:185 [1992]; Y. Matsui el al., Nature 353:750 [1991]). They migrate from the yolk sac epithelium through the hindgut endoderm to the genital ridges and proliferate through mitotic division to populate the testis.

At sexual maturity the spermatogonium goes through 5 or 6 mitotic divisions before it enters meiosis. The primitive spermatogonial stem cells (Ao/As) proliferate and form a population of intermediate spermatogonia types Apr, Aal, A1-4 after which they differentiate into type B spermatogonia. The type B spermatogonia differentiate to form primary spermatocytes which enter a prolonged meiotic prophase during which homologous chromosomes pair and recombine. The states of meiosis that are morphologically distinguishable are; preleptotene, leptotene, zygotene, pachytene, secondary spermatocytes and the haploid spermatids. Spermatids undergo great morphological changes during spermatogenesis, such as reshaping the nucleus, formation of the acrosome and assembly of the tail (A. R. Bellve et al, *Recovery, capacitation, acrosome reaction, and fractionation of sperm*, Methods Enzymol. 225:113–36 [1993]). The spermatocytes and spermatids establish vital contacts with the Sertoli cells through unique hemi-junctional attachments with the Sertoli cell membrane. The final changes in the maturing spermatozoan take place in the genital tract of the female prior to fertilization.

Initially, attempts were made to produce transgenic animals by adding DNA to spermatozoa which were then used to fertilize mouse eggs in vitro. The fertilized eggs were then transferred to pseudopregnant foster females, and of the pups born, 30% were reported to be transgenic and express the transgene. Despite repeated efforts by others, however, this experiment could not be reproduced and no transgenic pups were obtained. Indeed, there remains little doubt that the transgenic animals reputed to have been obtained by this method were not transgenic at all and the DNA incorporation reported was mere experimental artifact. Data collected from laboratories around the world engaged in testing this method showed that no transgenics were obtained from a total of 890 pups generated.

In summary, it is currently possible to produce live transgenic progeny but the available methods are costly and extremely inefficient. Spermatogenic transfection in accordance with this invention, either in vitro or in vivo, provides a simple, less costly and less invasive method of producing transgenic animals and one that is potentially highly effective in transferring allogeneic as well as xenogeneic genes into the animal's germ cells.

To facilitate in vitro transfection of male germ cells and implantation into a testis of a recipient male vertebrate it is advantageous first to depopulate the testis of the recipient vertebrate of untransfected male germ cells before transferring transfected male germ cells into it.

Depopulation of testis has commonly been done by exposing the whole vertebrate to gamma irradiation (X-ray), or localizing irradiation to the testis. (E.g., G. Pinon-Lataillade et al., *Endocrinological and histological changes induced by continuous low dose gamma-irradiation of rat testis*, Acta Endocrinol. (Copenh) 109(4):558–62 [1985]; G. Pinon-Lataillade and J. Maas, *Continuous gamma-irradiation of rats: dose-rate effect on loss and recovery of spermatogenesis*, Strahlentherapie 161(7):421–26 [1985]; C. R. Hopkinson et al., *The effect of local testicular irradiation on testicular histology and plasma hormone levels in the male rat*, Acta Endocrinol. (Copenh) 87(2):413–23 [1978]; G. Pinon-Lataillade et al, *Influence of germ cells upon Sertoli cells during continuous low-dose rate gamma-irradiation of adult rats*, Mol. Cell Endocrinol. 58(1):51–63 [1988]; P. Kamtchouing et al, *Effect of continuous low-dose rate gamma-irradiation on rat Sertoli cell function*, Reprod. Nutr. Dev. 28(4B):1009–17 [1988]; C. Pineau et al, *Assessment of testicular function after acute and chronic irradiation: further evidence for influence of late spermatids on Sertoli cell function in the adult rat*, Endocrinol. 124(6): 2720–28 [1989]; M. Kangasniemi et al., *Cellular regulation of basal and FSH-stimulated cyclic AMP production in irradiated rat testes*, Anat. Rec. 227(1):32–36 [1990]; G. Pinon-Lataillade et al, *Effect of an acute exposure of rat testes to gamma rays on germ cells and on Sertoli and Leydig cell functions*, Reprod. Nutr. Dev. 31(6):617–29 [1991]).

The mechanism of gamma radiation-induced spermatogonial degeneration is thought to be related to the process of apoptosis. (M. Hasegawa et al., *Resistance of differentiating spermatogonia to radiation-induced apoptosis and loss in p53-deficient mice*, Radiat. Res.149:263–70 [1998]).

Another method of depopulating a vertebrate testis is by administering a composition containing an alkylating agent, such as busulfan (Myleran). (E.g., F. X. Jiang, *Behaviour of spermatogonia following recovery from busulfan treatment in the rat*, Anat. Embryol. 198(1):53–61 [1998]; L. D. Russell and R. L. Brinster, *Ultrastructural observations of spermatogenesi following transplantation of rat testis cells into mouse seminiferous tubules*, J. Androl. 17(6):615–27 [1996]; N. Boujrad et al, *Evolution of somatic and germ cell populations after busulfan treatment in utero or neonatal cryptochidism in the rat*, Andrologia 27(4):223–28 [1995]; R. E. Linder et al, *Endpoint of spermatotoxicity in the rat after short duration exposures to fourteen reproductive toxicants*, Reprod. Toxicol. 6(6):491–505 [1992]; F. Kasuga and M. Takahashi, *The endocrine function of rat gonads with reduced number of germ cells following biusulfan treatment*, Endocrinol. Jpn 33(1):105–15 [1986]).

Cytotoxic alkylating agents, such as busulfan, chlorambucil, cyclophosphamide, melphalan, or ethyl ethanesulfonic acid, are frequently used to kill malignant cells in cancer chemotherapy. (E.g., Andersson et al, Parenteral busutfan for treatment of malignant disease, U.S. Pat. Nos. 5,559,148 and 5,430,057; Stratford et al., Stimulation of stem cell growth by the bryostatins, U.S. Pat. No. 5,358,711; Luck et al., Treatment employing vasoconstrictive substances in combination with cytotoxic agents for introduction into cellular lesion, U.S. Pat. No. 4,978,332). Treatment of mice with busulfan (13 mg–40 mg/kg body wt.), was reported to deplete male germs cells in the testis; both stems cells and differentiating spermatogonia were killed; doses over 30 mg/kg body weight resulted in azoospermia for up to 56 days after treatment. (L. R. Bucci and M. L. Meistrich, *Effects of busulfan on murine spermatogenesis: cytotoxicity, sterility, sperm abnormalities and dominant lethal mutations*, Radiation Research 176:259–68 [1987]).

The present invention addresses the need for spermatogenic transfection, either in vitro or in vivo, that is highly effective in transferring allogeneic as well as xenogeneic genes into the animal's germ cells and in producing transgenic vertebrate animals. The present technology addresses the requirements of germ line and stem cell line gene therapies in humans and other vertebrate species, including the need for a superior method of depopulating a testis of untransfected male germ cells. The present technology is of great value in producing transgenic animals in large species as well as for repairing genetic defects that lead to male infertility. Male germ cells that have stably integrated the DNA are selectable.

These and other benefits and features of the present invention are described herein.

SUMMARY OF THE INVENTION

The present invention relates to the in vivo and ex vivo (in vitro) transfection of eukaryotic animal germ cells with a desired genetic material. Briefly, the in vivo method involves injection of genetic material together with a suitable vector directly into the testicle of the animal. In this method, all or some of the male germ cells within the testicle are transfected in situ, under effective conditions. The ex vivo method involves extracting germ cells from the gonad of a suitable donor or from the animal's own gonad, using a novel isolation method, transfecting or otherwise genetically altering them in vitro, and then returning them to the testis under suitable conditions where they will spontaneously repopulate it. The ex vivo method has the advantage that the transfected germ cells may be screened by various means before being returned to the testis to ensure that the transgene is incorporated into the genome in a stable state. Moreover, after screening and cell sorting only enriched populations of germ cells may be returned. This approach provides a greater chance of transgenic progeny after mating.

This invention also relates to a novel method for the isolation of spermatogonia, comprising obtaining spermatogonia from a mixed population of testicular cells by extruding the cells from the seminiferous tubules and gentle enzymatic disaggregation. The spermatogonia or stem cells which are to be genetically modified, may be isolated from a mixed cell population by a novel method including the utilization of a promoter sequence, which is only active in cycling spermatogonial stem cell populations, for example, B-Myb or a spermotogonia specific promoter, such as the c-kit promoter region, c-raf-1 promoter, ATM (ataxia-telangiectasia) promoter, RBM (ribosome binding motif) promoter, DAZ (deleted in azoospermia) promoter, XRCC-1 promoter, HSP 90 (heat shock gene) promoter, cyclin A1 promoter, or FRMI (from fragile X site) promoter, optionally linked to a reporter construct, for example, a construct encoding Green Fluorescent Protein ([GFP] or enhanced GFP [EGFP]), Yellow Fluorescent Protein, Blue Fluorescent Protein, a phycobiliprotein, such as phycoerythrin or phycocyanin, or any other protein which fluoresces under suitable wave-lengths of light, or encoding a light-emitting protein. These unique promoter sequences drive the expression of the reporter construct only in the cycling spermatogonia. The spermatogonia, thus, are the only cells in the mixed population which will express the reporter construct and they, thus, may be isolated on this basis. Transgenic cells expressing a fluorescent or luminescent reporter construct can be sorted with the aid of, for example, a flow activated cell sorter (FACS) set at the appropriate wavelength or they may be selected by chemical methods.

The invention also relates to an effective method of substantially depopulating a vertebrate testis of male germ cells. The method involves administering a combination of a dose of an alkylating agent, such as busulfan, and a dose of gamma radiation to a vertebrate animal in an amount sufficient to substantially depopulate the vertebrate testis, to prepare it for implantation of male germ cells from a donor animal, for example. This combined treatment with an alkylating agent and gamma irradiation yields histologically superior results in eliminating the population of native untransfected or genetically unaltered male germ cells, compared to either an alkylating agent or gamma irradiation alone. Therefore, the present method of depopulating a vertebrate testis maximizes the production of transgenic animals using the present in vitro method of incorporating a polynucleotide encoding a desired trait or product into a maturing male germ cell.

This invention also relates to the repopulation of a testis with germ cells that have been isolated from a fresh or frozen testicular biopsy. These germ cells may or may not be genetically manipulated prior to implantation into a recipient testis.

For transfection (i.e., gene delivery), the method of the invention comprises administering to the animal, or to germ cells in vitro, a composition comprising amounts of nucleic acid comprising polynucleotides encoding a desired trait or product. In addition, the composition comprises, for example, a relevant controlling promoter region made up of nucleotide sequences. This is combined with, for example, a gene delivery system comprising a cell transfection promotion agent such as retro viral vectors, adenoviral and adenoviral related vectors, or liposomal reagents or other agents used for gene therapy. These introduced under conditions effective to deliver the nucleic acid segments to the animal's germ cells optionally with the polynucleotide inserted into the genome of the germ cells. Following incorporation of the DNA, the treated animal is either allowed to breed naturally, or reproduced with the aid of assisted reproductive technologies, and the progeny selected for the desired trait.

This technology is applicable to the production of transgenic animals for use as animal models, and to the modification of the genome of an animal, including a human, by addition, modification, or subtraction of genetic material, often resulting in phenotypic changes. The present methods are also applicable to altering the carrier status of an animal, including a human, where that individual is carrying a gene for a recessive or dominant gene disorder, or where the individual is prone to pass a multigenic disorder to his offspring.

A preparation suitable for use with the present methods comprises a polynucleotide segment encoding a desired trait and a transfection promotion agent, and optionally an uptake promotion agent which is sometime equipped with agents protective against DNA breakdown. The different components of the transfection composition are also provided in the form of a kit, with the components described above in measured form in two or more separate containers. The kit generally contains the different components in separate containers. Other components may also be provided in the kit as well as a carrier.

BRIEF DESCRIPTION OF THE DRAWINGS

FIG. 1 shows sections (400× magnification) of H&E-stained mouse (C57BL/6J strain) testis treated with a combination of gamma irradiation and busulfan (busulfan/400 Rad treatment).

FIG. 2 shows a histologic comparison of three different methods of depopulating a vertebrate testis of male germ cells and control. Shown are sections (400× magnification) of H&E-stained mouse (C57BL/6J strain) testes sampled two months after treatment.

FIG. 3 shows gene delivery to mouse testicular cells in vivo using a lentiviral vector. Images (400× magnification) were collected on a Zeiss 310 confocal light microscope. The HIV-based lentiviral vector contained the gene encoding GFP under the control of the CMV promoter.

DESCRIPTION OF THE PREFERRED EMBODIMENTS

Figure 1A:
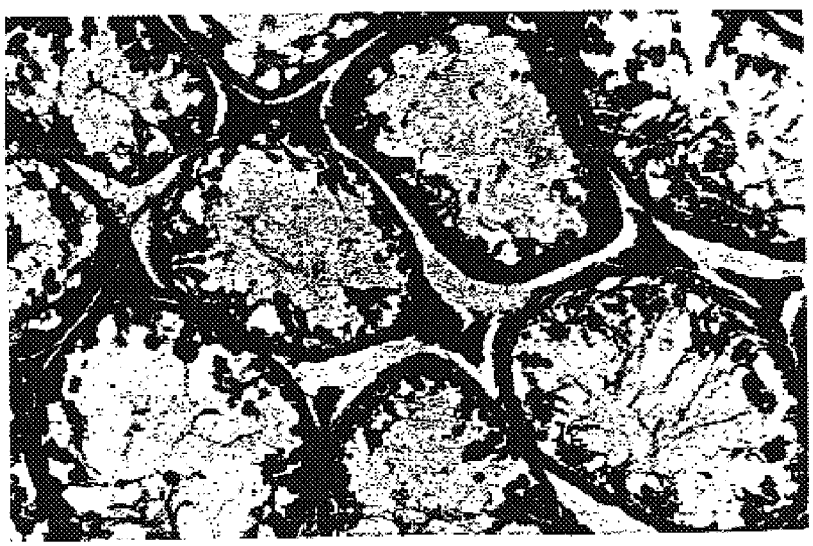
FIG. 1A shows several sectioned seminiferous tubules from a mouse two weeks after busulfan/400 Rad treatment.

The present invention arose from a desire by the present inventors to improve on existing methods for the genetic modification of an animal's germ cells and for producing transgenic animals. The pre-existing art methods rely on direct injection of DNA into zygotes produced in vitro or in vivo, or by the production of chimeric embryos using embryonal stem cells incorporated into a recipient blastocyst. Following this, such treated embryos are transferred to the primed uterus or oviduct. The available methods are extremely slow and costly, rely on several invasive steps, and only produce transgenic progeny sporadically and unpredictably.

In their search for a less costly, faster, and more efficient approach for producing transgenics, the present inventors devised the present method which relies on the in vivo or ex vivo (in vitro) transfection of male animal germ cells with a nucleic acid segment encoding a desired trait. The present method relies on at least one of the following strategies. A first method delivers the nucleic acid segment using known gene delivery systems in situ to the gonad of the animal (in vivo transfection), allows the transfected germ cells to differentiate in their own milieu, and then selects for animals exhibiting the nucleic acid's integration into its germ cells (transgenic animals). The thus selected animals may be mated, or their sperm utilized for insemination or in vitro fertilization to produce transgenic progeny. The selection may take place after biopsy of one or both gonads, or after examination of the animal's ejaculate amplified by the polymerase chain reaction to confirm the incorporation of the desired nucleic acid sequence. In order to simplify the confirmation of the actual incorporation of the desired nucleic acid, the initial transfection or gene delivery can include a co-transfected reporter gene, such as a gene encoding Green Fluorescent Protein (or encoding enhanced Green Fluorescent Protein [EGFP]), Yellow Fluorescent Protein, Blue Fluorescent Protein, a phycobiliprotein, such as phycoerythrin or phycocyanin, or any other protein which fluoresces under a suitable wave-length, or encoding a light-emitting protein.

Alternatively, male germ cells may be isolated from a donor animal and transfected or genetically altered in vitro to impart the desired trait. Following this genetic manipulation, germ cells which exhibit any evidence that the DNA has been modified in the desired manner are selected, and transferred to the testis of a suitable recipient animal. Further selection may be attempted after biopsy of one or both gonads, or after examination of the animal's ejaculate amplified by the polymerase chain reaction to confirm whether the desired nucleic acid sequence was actually incorporated. As described above, the initial transfection or gene delivery may have included a reporter gene, such as a gene encoding the Green Fluorescent Protein (or enhanced Green Fluorescent Protein [EGFP]), Yellow Fluorescent Protein, Blue Fluorescent Protein, a phycobiliprotein, such as phycoerythrin or phycocyanin, or any other protein which fluoresces under light of suitable wave-lengths, or encoding a light-emitting protein.

Another preferred reporter gene suitable for some applications is a gene encoding a protein that can enzymatically lead to the emission of light from a substrate(s); for purposes of the present invention, such a protein is a "light-emitting protein." For example, a light-emitting protein includes proteins such as luciferase or apoaequorin.

Before transfer of the germ cells, the recipient testis are generally treated in one, or a combination, of a number of ways to inactivate or destroy endogenous germ cells i.e., depopulate the testis of endogenous male germ cells. This is done by any suitable means, including by gamma irradiation, by chemical treatment, by means of infectious agents such as viruses, or by autoimmune depletion or by combinations thereof. Depopulation of the endogenous male germ cells facilitates the colonization of the recipient testis by the genetically altered donor cells.

Whatever means of depopulating the testis of endogenous male germ cells is used, the basic rigid architecture of the gonad should not be destroyed, nor badly damaged. If there is disruption of the fine system of tubule formation, it may be impossible for the exogenous spermatogonia to repopulate the testis. Disruption of tubules would also presumably lead to impaired transport of testicular sperm and result in infertility. Any controlled testicular injury of this kind should also be limited so that the Sertoli cells are not irreversibly damaged, as they are needed to provide a base for development of the germ cells during maturation. Moreover they may play a role in preventing the host immune defense system from destroying grafted foreign spermatogonia.

Most preferably, depopulation of the recipient testis of endogenous male germ cells is accomplished by using a method of substantially depopulating a vertebrate testis, to which the present invention is related. The present method of substantially depopulating a vertebrate testis is directed to a treatment with a cytotoxic alkylating agent, such as, but not limited to, busulfan (1,4-butanediol dimethanesulphonate; Myleran, Glaxo Wellcome), chlorambucil, cyclophosphamide, melphalan, or ethyl ethanesulfonic acid, combined with gamma irradiation, to be administered in either sequence. The combination of a dose of an alkylating agent and a dose of gamma radiation yields unexpectedly superior results in depopulating the testes of germ cells, compared to either treatment alone. The dose of the alkylating agent and the dose of gamma radiation are in an amount sufficient to substantially depopulate the testis.

The preferred dose of alkylating agent is about 4 to 10 milligrams per kilogram of body weight, and about 6 to 8 milligrams per kilogram of body weight is most preferred. The alkylating agent can be administered by any pharmaceutically acceptable delivery system, including but not limited to, intraperitoneal, intravenous, or intramuscular injection, intravenous drip, implant, transdermal or transmucosal delivery systems.

A recovery period between the administration of alkylating agent and irradiation is not essential, and the two treatments are most preferably done within zero to 24 hours of each other. Preferably, the time between the two treatments should not exceed 2 weeks, because this yields less than optimal results for purposes of transferring genetically modified or heterologous male germ cells to recipient testes.

The recipient vertebrate is gamma irradiated with a dose of about 200 to 800 Rads, most preferably about 350 to 450 Rads, directed locally to the testis to be depopulated. Less than 200 Rad yields little effect; greater than 800 Rad commonly produces symptoms of radiation sickness, particularly in the gastrointestinal tract. Within 3 days to 2 months after treatment to depopulate the recipient testis(es) in accordance with the present method, male germ cells can be transferred thereto as described herein. Prior to three days, traces of cytotoxic alkylating agent or endogenous apoptotic signal molecules may remain in the recipient testis to harm the male germ cells transferred thereto. After two months, the endogenous population of male germ cells will typically begin to restablish itself, yielding less than optimal results when transfected, genetically altered, or heterologous male germ cells are transferred to a recipient testes for breeding purposes.

Animals that were shown to carry suitably modified sperm cells then may be either allowed to mate naturally, or alternatively their spermatozoa are used. for insemination or in vitro fertilization. The thus obtained transgenic progeny may be bred, whether by natural mating or artificial insemination, to obtain further transgenic progeny. The method of this invention has a lesser number of invasive procedures than other available methods, and a high rate of success in producing incorporation into the progeny's genome of the nucleic acid sequence encoding a desired trait.

Primordial germ cells are thought to arise from the embryonic ectoderm, and are first seen in the epithelium of the endodermal yolk sac at the E8 stage. From there they migrate through the hindgut endoderm to the genital ridges. The primitive spermatogonial stem cells, known as A0/As, differentiate into type B spermatogonia. The latter further differentiate to form primary spermatocytes, and enter a prolonged meiotic prophase during which homologous chromosomes pair and recombine. Several morphological stages of meiosis are distinguishable: preleptotene, leptotene, zygotene, pachytene, secondary spermatocytes, and the haploid spermatids. The latter undergo further morphological changes during spermatogenesis, including the reshaping of their nucleus, the formation of acrosome, and assembly of the tail. The final changes in the spermatozoon take place in the genital tract of the female, prior to fertilization. The uptake of the nucleic acid segment administered by the present in vivo method to the gonads will reach germ cells that are at one or more of these stages, and be taken up by those that are at a more receptive stage. In the ex vivo (in vitro) method of genetic modification, generally only diploid spermatogonia are used for nucleic acid modification. The cells may be modified in vivo using gene therapy techniques, or in vitro using a number of different transfection strategies.

The inventors are, thus, providing in this patent a novel and unobvious method for; isolation of male germ cells, and for the in vivo and ex vivo (in vitro) transfection (or gene delivery) of allogeneic as well as xenogeneic DNA into an animal's germ cells. This comprises the administration to an animal of a composition comprising a gene delivery system and at least one nucleic acid segment, in amounts and under conditions effective to modify the animal's germ cells, and allowing the nucleic acid segment to enter, and be released into, the germ cells, and to integrate into their genome.

The in vivo introduction of the gene delivery mixture to the germ cells may be accomplished by direct delivery into the animal's testis(es), where it is distributed to male germ cells at various stages of development. The in vivo method utilizes novel technology, such as injecting the gene delivery mixture either into the vasa efferentia, directly into the seminiferous tubules, or into the rete testis using, for example, a micropipette. To ensure a steady infusion of the gene delivery mixture, under pressures which will not damage the delicate tubule system in the testis, the injection may be made through the micropipette with the aid of a picopump delivering a precise measured volume under controlled amounts of pressure. The micropipette may be made of a suitable material, such as metal or glass, and is usually made from glass tubing which has been drawn to a fine bore at its working tip, e.g. using a pipette puller. The tip may be angulated in a convenient manner to facilitate its entry into the testicular tubule system. The micropipette may be also provided with a beveled working end to allow a better and less damaging penetration of the fine tubules at the injection site. This bevel may be produced by means of a specially manufactured grinding apparatus. The diameter of the tip of the pipette for the in vivo method of injection may be about 15 to 45 microns, although other sizes may be utilized as needed, depending on the animal's size. The tip of the pipette may be introduced into the rete testis or the tubule system of the testicle, with the aid of a binocular microscope with coaxial illumination, with care taken not to damage the wall of the tubule opposite the injection point, and keeping trauma to a minimum. On average, a magnification of about ×25 to ×80 is suitable, and bench mounted micromanipulators are not severally required as the procedure may be carried out by a skilled artisan without additional aids. A small amount of a suitable, non-toxic dye, may be added to the gene delivery fluid to confirm delivery and dissemination to the tubules of the testis. It may include a dilute solution of a suitable, non-toxic dye, which may be visualized and tracked under the microscope.

In this manner, the gene delivery mixture is brought into intimate contact with the germ cells. The gene delivery mixture typically comprises the modified nucleic acid encoding the desired trait, together with a suitable promoter sequence, and optionally agents which increase the uptake of the nucleic acid sequence, such as liposomes, retroviral vectors, adenoviral vectors, adenovirus enhanced gene delivery systems, or combinations thereof A reporter construct such as the gene encoding for Green Fluorescent Protein may further be added to the gene delivery mixture. Targeting molecules such as c-kit ligand may be added to the gene delivery mixture to enhance the transfer of the male germ cell.

For the ex vivo (in vitro) method of genetic alteration, the introduction of the modified germ cells into the recipient testis may be accomplished by direct injection using a suitable micropipette. Support cells, such as Leydig or Sertoli cells that provide hormonal stimulus to spermatogonial differentiation, may be transferred to a recipient testis along with the modified germ cells. These transferred support cells may be unmodified, or, alternatively, may themselves have been transfected, together with- or separately from the germ cells. These transferred support cells may be autologous or heterologous to either the donor or recipient testis. A preferred concentration of cells in the transfer fluid may easily be established by simple experimentation, but will likely be within the range of about $1 \times 10^5 – 10 \times 10^5$ cells per 10 $\mu$l of fluid. This micropipette may be introduced into the vasa efferentia, the rete testis or the seminiferous tubules, optionally with the aid of a picopump to control pressure and/or volume, or this delivery may be done manually. The micropipette employed is in most respects similar to that used for the in vivo injection, except that its tip diameter generally will be about 70 microns. The microsurgical method of introduction is similar in all respects to that used for the in vivo method described above. A suitable dyestuff may also be incorporated into the carrier fluid for easy identification of satisfactory delivery of the transfected germ cells.

The transfected germ cells are preferably transferred to a testis of a recipient animal, which can be, but need not be, the same donor animal. The testis of the donor animal are preferably depopulated of native germ cells before transfected germ cells are transferred into it. This depopulation can be done by any suitable means. But vertebrate testes are most preferably depopulated by a combined treatment of the animal with an alkylating agent and gamma irradiation in accordance with the present method of substantially depopulating a vertebrate testes. Donor male germ cells can then be transferred to the recipient male.

Once in contact with germ cells, whether they are in situ in the animal or vitro, the gene delivery mixture facilitates the uptake and transport of the xenogeneic genetic material into the appropriate cell location for integration into the genome and expression. A number of known gene delivery methods may be used for the uptake of nucleic acid sequences into the cell.

"Gene delivery (or transfection) mixture", in the context of this patent, means selected genetic material together with an appropriate vector mixed, for example, with an effective amount of lipid transfecting agent. The amount of each component of the mixture is chosen so that the transfection or genetic alteration of a specific species of germ cell is optimized. Such optimization requires no more than routine experimentation. The ratio of DNA to lipid is broad, preferably about 1:1, although other proportions may also be utilized depending on the type of lipid agent and the DNA utilized. This proportion is not crucial.

"Transfecting agent", as utilized herein, means a composition of matter added to the genetic material for enhancing the uptake of exogenous DNA segment(s) into a eukaryotic cell, preferably a mammalian cell, and more preferably a mammalian germ cell. The enhancement is measured relative to the uptake in the absence of the transfecting agent. Examples of transfecting agents include adenovirus-transferrin-polylysine-DNA complexes. These complexes generally augment the uptake of DNA into the cell and reduce its breakdown during its passage through the cytoplasm to the nucleus of the cell. These complexes may be targeted to the male germ cells using specific ligands which are recognized by receptors on the cell surface of the germ cell, such as the c-kit ligand or modifications thereof.

Other preferred transfecting agents include lipofectin, lipfectamine, DIMRIE C, Superfect, and Effectin (Qiagen). Although these are not as efficient transfecting agents as viral transfecting agents, they have the advantage that they facilitate stable integration of xenogeneic DNA sequence into the vertebrate genome, without size restrictions commonly associated with virus-derived transfecting agents.

"Virus", as used herein, means any virus, or transacting fragment thereof, which may facilitate the delivery of the genetic material into male germ cells. Examples of viruses which are suitable for use herein are adenoviruses, adeno-associated viruses, retroviruses such as human immune-deficiency virus, Moloney murine leukemia virus and the retrovirus vector derived from Moloney virus called vesicular-stomatitis-virus-glycoprotein (VSV-G)-Moloney murine leukemia virus, mumps virus, and transfecting fragments of any of these viruses, and other viral DNA segments that facilitate the uptake of the desired DNA segment by, and release into, the cytoplasm of germ cells and mixtures thereof. The mumps virus is particularly suited because of its affinity for immature sperm cells including spermatogonia. All of the above viruses may require modification to render them non-pathogenic or less antigenic. Other known vector systems, however, may also be utilized within the confines of the invention.

"Genetic material", as used herein, means DNA sequences capable of imparting novel genetic modification (s), or biologically functional characteristic(s) to the recipient animal. The novel genetic modification(s) or characteristic(s) may be encoded by one or more genes or gene segments, or may be caused by removal or mutation of one or more genes, and may additionally contain regulatory sequences. The transfected genetic material is preferably functional, that is it expresses a desired trait by means of a product or by suppressing the production of another. Examples of other mechanisms by which a gene's function may be expressed are genomic imprinting, i.e. inactivation of one of a pair of genes (alleles) during very early embryonic development, or inactivation of genetic material by mutation or deletion of gene sequences, or by repression of a dominant negative gene product, among others.

In addition, novel genetic modification(s) may be artificially induced mutations or variations, or natural allelic mutations or variations of a gene(s). Mutations or variations may be induced artificially by a number of techniques, all of which are well known in the art, including chemical treatment, gamma irradiation treatment, ultraviolet radiation treatment, ultraviolet radiation, and the like. Chemicals useful for the induction of mutations or variations include carcinogens such as ethidium bromide and others known in the art.

DNA segments of specific sequences may also be constructed to thereby incorporate any desired mutation or variation or to disrupt a gene or to alter genomic DNA. Those skilled in the art will readily appreciate that the genetic material is inheritable and is, therefore, present in almost every cell of future generations of the progeny, including the germ cells. Among novel characteristics are the expression of a previously unexpressed trait, augmentation or reduction of an expressed trait, over expression or under expression of a trait, ectopic expression, that is expression of a trait in tissues where it normally would not be expressed, or the attenuation or elimination of a previously expressed trait. Other novel characteristics include the qualitative change of an expressed trait, for example, to palliate or alleviate, or otherwise prevent expression of an inheritable disorder with a multigenic basis.

For the expression of transfected or otherwise delivered genetic material to obtain a desired trait, a promoter sequence is operably linked to a polynucleotide sequence encoding the desired trait or product. For purposes of the present invention, "operatively linked" means that the promoter sequence, is located upstream from the coding sequence and that both sequences are oriented in a 5' to 3' manner, such that transcription could take place in vitro in the presence of all essential enzymes, transcription factors, co-factors, activators, and reactants, under favorable physical conditions, e.g., suitable pH and temperature. This does not mean that, in any particular cell, conditions will favor transcription.

A promoter sequence is chosen that operates in the cell type of interest. A promoter sequence, which is only active in cycling spermatogonial stem cell populations can be used for differential expression in male germ cells, for example, B-Myb or a spermotogonia specific promoter, such as the c-kit promoter region, c-raf-1 promoter, ATM (ataxia-telangiectasia) promoter, RBM (ribosome binding motif) promoter, DAZ (deleted in azoospermia) promoter, XRCC-1 promoter, HSP 90 (heat shock gene) promoter, or FRMI (from fragile X site) promoter.

A human cyclin A1 promoter region, a non-human homologue or an operative fragment thereof, is a most preferred promoter sequence for driving the expression of a reporter construct or for driving the expression of another desired xenogeneic gene sequence, when expression is desired in germ cells, hematopoietic cells, or other stem cells of a vertebrate. (C. Müller et al., J. Biol. Chem. 274(16): 11220–28 [Apr. 16, 1999]).

The present invention also relates to a kit for transfecting or otherwise genetically altering a male vertebrate's germ cells, which is useful for obtaining transgenic male germ cells. The kit is a ready assemblage of materials for facilitating the transfection or genetic alteration of a vertebrate male germ cell. A kit of the present invention contains a transfecting (or gene delivery) agent, as described above, and an alkylating agent for use in substantially depopulating a vertebrate testis in accordance with the present method of depopulating a vertebrate testis, together with instructions for using the components effectively.

Optionally, the kit contains a radiation shield capable of specifically directing gamma irradiation to a testis. The shield contains lead or another dense material that tends to absorb gamma radiation, and the shield has slots, holes, tubes or other suitable means for selectively directing gamma radiation to the testis of a male vertebrate.

Optionally, the kit contains a polynucleotide that includes a promoter sequence operatively linked to a DNA sequence encoding a reporter gene, preferably a fluorescent or light-emitting protein as described above. Optionally, the kit includes an immunosuppressing agent, such as cyclosporin or a corticosteroid, and/or an additional nucleotide sequence encoding for the expression of a desired trait. The materials or components assembled in the kit are provided to the practitioner stored in any convenient and suitable way that preserves their operability and utility. For example the components can be in dissolved, dehydrated, or lyophilized form; they can be provided at room, refrigerated or frozen temperatures.

This invention also relates to a method for the isolation of spermatogonia, comprising obtaining spermatogonia from a mixed population of testicular cells by extruding the cells from the seminiferous tubules and gentle enzymatic disaggregation. The spermatogonia or stem cells which are to be genetically modified, may be isolated from a mixed cell population by a novel method including the utilization of a promoter sequence, which is only active in stem cells, such as human cyclin A1 promoter, or in cycling spermatogonial stem cell populations, for example, B-Myb or a spermotogonia specific promoter, such as the c-kit promoter region, c-raf-1 promoter, ATM (ataxia-telangiectasia) promoter, RBM (ribosome binding motif) promoter, DAZ (deleted in azoospermia) promoter, XRCC-1 promoter, HSP 90 (heat shock gene) promoter, or FRMI (from fragile X site) promoter, linked to a reporter construct, for example, a construct comprising a gene encoding Green Fluorescent Protein (or EGFP), Yellow Fluorescent Protein, Blue Fluorescent Protein, a phycobiliprotein, such as phycoerythrin or phycocyanin, or any other protein which fluoresces under suitable wave-lengths of light, or encoding a light-emitting protein, such as luciferase or apoaequorin. These unique promoter sequences drive the expression of the reporter construct only in the cycling spermatogonia. The spermatogonia, thus, are the only cells in the mixed population which will express the reporter construct(s) and they, thus, may be isolated on this basis. In the case of a fluorescent reporter construct, the cells may be sorted with the aid of, for example, a FACS set at the appropriate wavelength(s) or they may be selected by chemical methods.

The method of the invention is suitable for application to a variety of vertebrate animals, all of which are capable of producing gametes, i.e. sperm or ova. Thus, in accordance with the invention novel genetic modification(s) and/or characteristic(s) may be imparted to animals, including mammals, such as humans, non-human primates, for example simians, marmosets, domestic agricultural animals such as sheep, cows, pigs, horses, particularly race horses, marine mammals, feral animals, rodents such as mice and rats, gerbils, hamsters, rabbits, and the like. Other animals include fowl such as chickens, turkeys, ducks, ostriches, emus, geese, guinea fowl, doves, quail, rare and ornamental birds, and the like. Of particular interest are endangered species of wild animal, such rhinoceros, tigers, cheetahs, certain species of condor, and the like.

Broadly speaking, a "transgenic" animal is one that has had foreign DNA permanently introduced into its cells. The foreign gene(s) which (have) been introduced into the animal's cells is (are) called a "transgene(s)". The present invention is applicable to the production of transgenic animals containing xenogeneic, i.e., exogenous, transgenic genetic material, or material from a different species, including biologically functional genetic material, in its native, undisturbed form in which it is present in the animal's germ cells. In other instances, the genetic material is "allogeneic" genetic material, obtained from different strains of the same species, for example, from animals having a "normal" form of a gene, or a desirable allele thereof. Also the gene may be a hybrid construct consisting of promoter DNA sequences and DNA coding sequences linked together. These sequences may be obtained from different species or DNA sequences from the same species that are not normally juxtaposed. The DNA construct may also contain DNA sequences from prokaryotic organisms, such as bacteria, or viruses.

In one preferred embodiment, the transfected germ cells of the transgenic animal have the non-endogenous (exogenous) genetic material integrated into their chromosomes. This is what is referred to as a "stable transfection". This is applicable to all vertebrate animals, including humans. Those skilled in the art will readily appreciate that any desired traits generated as a result of changes to the genetic material of any transgenic animal produced by this invention are inheritable. Although the genetic material was originally inserted solely into the germ cells of a parent animal, it will ultimately be present in the germ cells of future progeny and subsequent generations thereof. The genetic material is also present in the differentiated cells, i.e. somatic cells, of the progeny. This invention also encompasses progeny resulting from breeding of the present transgenic animals. The transgenic animals bred with other transgenic or non-transgenic animals of the same species will produce some transgenic progeny, which should be fertile. This invention, thus, provides animal line(s) which result from breeding of the transgenic animal(s) provided herein, as well as from breeding their fertile progeny.

"Breeding", in the context of this patent, means the union of male and female gametes so that fertilization occurs. Such a union may be brought about by natural mating, i.e. copulation, or by in vitro or in vivo artificial means. Artificial means include, but are not limited to, artificial insemination, in vitro fertilization, cloning and embryo transfer, intracytoplasmic spermatozoal microinjection, cloning and embryo splitting, and the like. However, others may also be employed.

The transfection of mature male germ cells may be also attained utilizing the present technology upon isolation of the cells from a vertebrate, as is known in the art, and exemplified in Example 10. The thus isolated cells may then be transfected ex vivo (in vitro), or cryopreserved as described in Example 11. The actual transsection of the isolated testicular cells may be accomplished, for example, by isolation of a vertebrate's testes, decapsulation and teasing apart and mincing of the seminiferous tubules. The separated cells may then be incubated in an enzyme mixture comprising enzymes known for gently breaking up the tissue matrix and releasing undamaged cells such as, for example, pancreatic trypsin, collagenase type I, pancreatic DNAse type I, as well as bovine serum albumin and a modified DMEM medium. The cells may be incubated in the enzyme mixture for a period of about 5 min to about 30 min, more preferably about 15 to about 20 min, at a temperature of about 33° C. to about 37° C., more preferably about 36 to 37° C. After washing the cells free of the enzyme mixture, they may be placed in an incubation medium such as DMEM, and the like, and plated on a culture dish. Any of a number of commercially available transfection mixtures may be admixed with the polynucleotide encoding a desire trait or product for transfection of the cells. The transfection mixture may then be admixed with the cells and allowed to interact for a period of about 2 hrs to about 16 hrs, preferably about 3 to 4 hrs, at a temperature of about 33° C. to about 37° C., preferably about 36° C. to 37° C., and more preferably in a constant and/or controlled atmosphere. After this period, the cells are preferably placed at a lower temperature of about 33° C. to about 34° C., preferably about 30–35° C. for a period of about 4 hrs to about 20 hrs, preferably about 16 to 18 hrs. Other conditions which do not deviate radically from the ones described may also be utilized as an artisan would know.

The present method is applicable to the field of gene therapy, since it permits the introduction of genetic material encoding and regulating specific genetic traits. Thus, in the human, for example, by treating parents it is possible to correct many single gene disorders which otherwise might affect their children. It is similarly possible to alter the expression of fully inheritable disorders or those disorders having at least a partially inherited basis, which are caused by interaction of more than one gene, or those which are more prevalent because of the contribution of multiple genes. This technology may also be applied in a similar way to correct disorders in animals other than human primates. In some instances, it may be necessary to introduce one or more "gene(s)" into the germ cells of the animal to attain a desired therapeutic effect, as in the case where multiple genes are involved in the expression or suppression of a defined trait. In the human, examples of multigenic disorders include diabetes mellitus caused by deficient production of, or response to, insulin, inflammatory bowel disease, certain forms of atheromatus cardiovascular disease and hypertension, schizophrenia and some forms of chronic depressive disorders, among others. In some cases, one gene may encode an expressible product, whereas another gene encodes a regulatory function, as is known in the art. Other examples are those where homologous recombinant methods are applied to repair point mutations or deletions in the genome, inactivation of a gene causing pathogenesis or disease, or insertion of a gene that is expressed in a dominant negative manner, or alterations of regulating elements such as gene promoters, enhancers, the untranslated tail region of a gene, or regulation of expansion of repeated sequences of DNA which cause such diseases as Huntingdon's chorea, Fragile-X syndrome and the like.

A specific reproductive application of the present method is to the treatment of animals, particularly humans, with disorders of spermatogenesis. Defective spermatogenesis or spermiogenesis frequently has a genetic basis, that is, one or mutations in the genome may result in failure of production of normal sperm cells. This may happen at various stages of the development of germ cells, and may result in male infertility or sterility. The present invention is applicable, for example, to the insertion or incorporation of nucleic acid sequences into a recipient's genome and, thereby, establish spermatogenesis in the correction of oligozoospermia or azoospermia in the treatment of infertility. Similarly, the present methods are also applicable to males whose subfertility or sterility is due to a motility disorder with a genetic basis.

The present method is additionally applicable to the generation of transgenic animals expressing agents which are of therapeutic benefit for use in human and veterinary medicine or well being. Examples include the production of pharmaceuticals in domestic cows' milk, such as factors which enhance blood clotting for patients with types of haemophilia, or hormonal agents such as insulin and other peptide hormones.

The present method is further applicable to the generation of transgenic animals of a suitable anatomical and physiological phenotype for human xenograft transplantation. Transgenic technology permits the generation of animals which are immune-compatible with a human recipient. Appropriate organs, for example, may be removed from such animals to allow the transplantation of, for example, the heart, lung and kidney.

In addition, germ cells transfected in accordance with this invention may be extracted from the transgenic animal, and stored under conditions effective for later use, as is known in the art. Storage conditions include the use of cryopreservation using programmed freezing methods and/or the use of cryoprotectants, and the use of storage in substances such as liquid nitrogen. The germ cells may be obtained in the form of a male animal's semen, or separated spermatozoa, or immature spermatocytes, or whole biopsies of testicular tissue containing the primitive germ cells. Such storage techniques are particularly beneficial to young adult humans or children, undergoing oncological treatments for such diseases such as leukemia or Hodgkin's lymphoma. These treatments frequently irreversibly damage the testicle and, thus, render it unable to recommence spermatogenesis after therapy by, for example, irradiation or chemotherapy. The storage of germ cells and subsequent testicular transfer allows the restoration of fertility. In such circumstances, the transfer and manipulation of germ cells as taught in this invention are accomplished, but transfection is generally not relevant or needed.

In species other than humans, the present techniques are valuable for transport of gametes as frozen germ cells. Such transport will facilitate the establishment of various valued livestock or fowl, at a remote distance from the donor animal. This approach is also applicable to the preservation of endangered species across the globe.

The invention will now be described in greater detail by reference to the following non-limiting examples. The pertinent portions of the contents of all references, and published patent applications cited throughout this patent necessary for enablement purposes are hereby incorporated by reference.

EXAMPLES

Transfection of Male Germ Cells in Vivo and in Vitro

In Vivo Adenovirus-enhanced Transferrin-polvlysine-mediated Delivery of Green Lantern Reporter Gene Delivery System to Testicular Cells The adenovirus enhanced transferrin-polylysine-mediated gene delivery system has been described and patented by Curiel et al. (Curiel D. T.,et al., Adenovirus enhancement of transferrin-polylysine-mediated gene delivery, PNAS USA 88: 8850–8854 (1991). The delivery of DNA depends upon endocytosis mediated by the transferrin receptor (Wagner et al., Transferrin-polycation conjugates as carriers for DNA uptake into cells, PNAS (USA) 87: 3410–3414 (1990). In addition this method relies on the capacity of adenoviruses to disrupt cell vesicles, such as endosomes and release the contents entrapped therein. This system can enhance the gene delivery to mammalian cells by as much as 2,000 fold over other methods.

The gene delivery system employed for the in vivo experiments was prepared as shown in examples below.

Example 1
Preparation of Transferrin-poly-L-Lysine Complexes

Human transferrin was conjugated to poly (L-lysine) using EDC (1-ethyl-3-(3-dimethyl aminopropyl carbodiimide hydrochloride) (Pierce), according to the method of Gabarek and Gergely (Gabarek & Gergely, Zero-length cross-linking procedure with the use of active esters, Analyt. Biochem 185: 131 (1990)). In this reaction, EDC reacts with a carboxyl group of human transferrin to form an amine-reactive intermediate. The activated protein was allowed to react with the poly (L-lysine) moiety for 2 hrs at room temperature, and the reaction was quenched by adding hydroxylamine to a final concentration of 10 mM. The conjugate was purified by gel filtration, and stored at $-20°$ C.

Example 2
Preparation of DNA for In Vivo Transfection

The Green Lantern-1 vector (Life Technologies, Gibco BRL, Gaithersberg, Md.) is a reporter construct used for monitoring gene transfection in mammalian cells. It consists of the gene encoding the Green Fluorescent Protein (GFP) driven by the cytomegalovirus (CMV) immediate early promoter. Downstream of the gene is a SV40 polyadenylation signal. Cells transfected with Green Lantern-1 fluoresce with a bright green light when illuminated with blue light. The excitation peak is 490 nm.

Example 3
Preparation of Adenoviral Particles

Adenovirus dI312, a replication-incompetent strain deleted in the Ela region, was propagated in the Ela trans-complementing cell line 293 as described by Jones and Shenk (Jones and Shenk, PNAS USA (1979) 79: 3665–3669). A large scale preparation of the virus was made using the method of Mittereder and Trapnell (Mittereder et al., "Evaluation of the concentration and bioactivity of adenovirus vectors for gene therapy", J. Urology, 70: 7498–7509 (1996)). The virion concentration was determined by UV spectroscopy, 1 absorbance unit being equivalent to 10 viral particles/ml. The purified virus was stored at $-70°$ C.

Example 4
Formation of Transferrin-poly-L Lysine-DNA-Viral Complexes

6 $\mu$g transferrin-polylysine complex from Example 1 were mixed in $7.3\times10^7$ adenovirus dI312 particles prepared as in Example 3, and then mixed with 5 $\mu$g of the Green Lantern DNA construct of Example 2, and allowed to stand at room temperature for 1 hour. About 100 $\mu$l of the mixture were drawn up into a micropipette, drawn on a pipette puller, and slightly bent on a microforge. The filled micropipette was then attached to a picopump (Eppendort), and the DNA complexes were delivered under continuous pressure, in vivo to mice as described in Example 6.

Controls were run following the same procedure, but omitting the transferrin-poly-lysine-DNA-viral complexes from the administered mixture.

Example 5
Comparison of Adenovirus-enhanced Transferrin-polylysine & Lipofectin Mediated Transfection Efficiency The conjugated adenovirus particle complexed with DNA were tested on CHO cells in vitro prior to in vivo testing. For these experiments a luciferase reporter gene was used due to the ease of quantifying luciferase activity. The expression construct consists of a reporter gene encoding luciferase, is driven by the CMV promoter (Invitrogen, Carlsbad, Calif. 92008). CHO cells were grown in Dulbecco's modified Eagle's medium (DMEM) with 10% fetal calf serum. For gene transfer experiments CHO cells were seeded into 6 cm tissue culture plates and grown to about 50% confluency ($5\times10^5$ cells). Prior to transfection the medium was aspirated and replaced with serum free DMEM. Cells were either transfected with transferrin-polylysine-DNA complexes or with lipofectin DNA aggregates. For the transferrin-polylysine mediated DNA transfer, the DNA-adenovirus complexes were added to the cells at a concentration of $0.05–3.2\times10^4$ adenovirus particles per cell. Plates were returned to the 5% $CO_2$ incubator for 1 hour at $37°$ C. After 1 hour 3 ml of complete media was added to the wells and the cells were allowed to incubate for 48 hours before harvesting. The cells were removed from the plate, counted and then lysed for measurement of luciferase activity.

For cells transfected by lipofectin, 1 $\mu$g of CMV-luciferase DNA was incubated with 17 $\mu$l of Lipofectin (Life Technologies). The DNA-lipofectin aggregates were added to the CHO cells and allowed to incubate at $37°$ C. at 5% $CO_2$ for 4 hours. Three milliliters of complete medium was added then to the cells and they were allowed to incubate for 48 hours. The cells were harvested, counted and lysed for luciferase activity. The luciferase activity was measured by a luminometer. The results obtained are shown in Table 1.

The data included in Table 1 below show that the adenovirus-enhanced transferrin-polylysine gene delivery system is 1,808 fold more efficient than lipofection for transfection of CHO cells.

TABLE 1

Comparison of Lipofection & Adenovirus Enhanced Transferrin-polylysine Transfection of CHO Cells

| Sample | Treatment | Luciferase Activity (RLU) |
|---|---|---|
| 1 | $1 \times 10^7$ particles + 6 ug CMV-Luc | 486 |
| 2 | $2.5 \times 10^7$ particles + 6 ug CMV-Luc | 1,201 |
| 3 | $5.0 \times 10^7$ particles + 6 ug CMV-luc | 11,119 |
| 4 | $1 \times 10^9$ particles + 6 ug CMV-Luc | 2,003,503 |
| 5 | Lipofection | 1,108 |
| 6 | Unmanipulated cells | 155 |

Example 6
In Vivo Delivery of DNA to Animal's Germ Cells via Transferrin-L-lysine-DNA-Viral Complexes The GFP DNA-transferrin-polylysine viral complexes, prepared as described in Example 4 above, were delivered into the seminiferous tubules of three (3)-week-old B6D2F1 male mice. The DNA delivery by transferrin receptor-mediated endocytosis is described by Schmidt et al. and Wagner et al. (Schmidt et al., Cell 4: 41–51 (1986); Wagner, E., et aL PNAS (1990), (USA) 81: 3410–3414 [1990]). In addition, this delivery system relies on the capacity of adenoviruses to disrupt cell vesicles, such as endosomes and release the contents entrapped therein. The transfection efficiency of this system is almost 2,000 fold higher than lipofection.

The male mice were anesthetized with 2% Avertin (100% Avertin comprises 10 g 2,2,2-tribromoethanol (Aldrich) and 10 ml t-amyl alcohol (Sigma), and a small incision made in their skin and body wall, on the ventral side of the body at the level of the hind leg. The animal's testis was pulled out through the opening by grasping at the testis fat pad with forceps, and the vas efferens tubules exposed and supported by a glass syringe. The GFP DNA-transferrin-polylysine viral complexes were injected into a single vasa efferentia using a glass micropipette attached to a hand held glass syringe or a pressurized automatic pipettor (Eppendorf), and Trypan blue added to visualize the entry of the mixture into the seminiferous tubules. The testes were then placed back in the body cavity, the body wall was sutured, the skin closed with wound clips, and the animal allowed to recover on a warm pad.

Example 7
Detection of DNA and Transcribed Message

Nine (9) days after delivery of the genetic material to the animals' testis, two of the animals were sacrificed, their testes removed, cut in half, and frozen in liquid nitrogen. The DNA from one half of the tissues, and the RNA from the other half of the tissues were extracted and analyzed.

(a) Detection of DNA

The presence of GFP DNA in the extracts was tested 9 days after administration of the transfection mixture using the polymerase chain reaction, and GFP specific oligonucleotides. GFP DNA was present in the testes of the animals that had received the DNA complexes, but was absent from sham operated animals.

(b) Detection of RNA

The presence of GFP mRNA was assayed in the testes of experimental animals as follows. RNA was extracted from injected, and non-injected testes, and the presence of the GFP messages was detected using reverse transcriptase PCR (RT PCR) with GFP specific primers. The GFP message was present in the injected testes, but not in the control testes. Thus, the DNA detected above by PCR analysis is, in fact, episomal GFP DNA, or GFP DNA which has integrated into the chromosomes of the animal. The transfected gene was being expressed.

Example 8
Expression of Non-endogenous DNA

Two males, one having received an injection with the GFP transfection mixture and a control to whom only surgery was administered, were sacrificed 4 days after injection, and their testes excised, and fixed in 4% paraformaldehyde for 18 hours at 4° C. The fixed testis was then placed in 30% sucrose in PBS with 2 mM $MgCl_2$ for 18 hours at 4° C., embedded in OCT frozen on dry ice, and sectioned. When the testes of both animals were examined with a confocal microscope with fluorescent light at a wavelength of 488 nM, bright fluorescence was detected in the tubules of the GFP-injected mice, but not in the testes of the controls. Many cells within the seminferous tubules of the GFP-injected mouse showed bright fluorescence, which evidences that they were expressing Fluorescent Green Protein.

Example 9
Generation of Offspring from Normal Matings

GFP transfected males were mated with normal females. The females were allowed to complete gestation, and the pups to be born. The pups (F1 offspring or progeny) were screened for the presence of the novel genetic material(s).

Example 10
In Vitro Transfection of Testicular Cells

Cells were isolated from the testes of three 10-day-old mice. The testes were decapsulated and the seminiferous tubules were teased apart and minced with sterile needles. The cells were incubated in enzyme mixture for 20 minutes at 37° C. The enzyme mixture was made up of 10 mg bovine serum albumin (embryo tested), 50 mg bovine pancreatic trypsin type III, Clostridium collagenase type I, 1 mg bovine pancreatic DNAse type I in 10 mls of modified HTF medium (Irvine Scientific, Irvine, Calif.). The enzymes were obtained from Sigma Company (St. Louis, Mo. 63178). After digestion, the cells were washed twice by centrifugation at 500×g with HTF medium and resuspended in 250 µl HTF medium. The cells were counted, and $0.5 \times 10^6$ cells were plated in a 60 mm culture dish in a total volume of 5 ml DMEM (Gibco-BRL, Life Technologies, Gaithesburg, Md. 20884). A transfection mixture was prepared by mixing 5 µg Green Lantern DNA (Gibco-BRL, Life Technologies, Gaithesburg, Md. 20884) with 20 µl Superfect (Qiagen, Santa Clarita, Calif. 91355) and 150 µl DMEM. The transfection mix was added to the cells and they were allowed to incubate for 3 hours at 37° C., 5% $CO_2$ The cells were transferred to a 33° C. incubator and incubated overnight.

The following morning the cells were assessed for transfection efficiency by counting the number of fluorescent cells. In this experiment the transfection efficiency was 90% (Figure not shown). The testicular cells transfected with Green Lantern viewed with Nomaski optics ×20 show the same cells viewed with FITC. Nearly all the cells were fluorescent, which is confirmation of their successful transfection.

Example 11
Preparation of a Cell Suspension from Testicular Tissue for Cryopreservation A cell suspension was prepared from mice of different ages as described below.

| | |
|---|---|
| Group I: | 7–10 day olds |
| Group II: | 15–17 day olds |
| Group III: | 24–26 day olds |

The mice's testes were dissected, placed in phosphate buffered saline (PBS) decapsulated, and the seminiferous tubules were teased apart. Seminiferous tubules from groups I and II were transferred to HEPES buffered culture medium (D-MEM) (Gibco-BRL, Life Technologies, Gaithersberg, Md. 20884) containing 1 mg/ml Bovine serum albumin (BSA) (Sigma, St. Louis, Mo. 63178) and Collagenase Type I (Sigma) for the removal of interstitial cells. After a 10 minute incubation at 33° C., the tubules were lifted into fresh culture medium. This enzymatic digestion was not carried out on the testes from group I because of their fragility.

The tubules from group II and III mice or the whole tissue from group I mice were transferred to a Petri dish with culture medium and were cut into 0.1–1 mm pieces using a sterile scalpel and needle. The minced tissue was centrifuged at 500×g for 5 minutes and the pellet was resuspended in 1 ml of enzyme mix. The enzyme mix was made up in D-DMEM with HEPES (Gibco-BRL) and consisted of 1 mg/ml bovine serum albumin (BSA) (Sigma, embryo tested), 1 mg/ml collagenase I (Sigma) and 5 mg/ml bovine pancreatic trypsin (Sigma) and 0.1 mg/ml deoxyribonuclease I (DN-EP, Sigma). The tubules were incubated in enzyme mix for 30 minutes at 33° C. After the incubation, 1 ml of medium was added to the mix and the cells were centrifuged at 500×g for 5 min. The cells were washed twice in medium by centrifugation and resuspension. After the final wash the cell pellet was resuspended in 250 µl of culture medium and counted.

Example 12
Transferring Transfected Male Germ Cells Into Recipient Testis

The cells were injected into the testis via the vasa efferentia using a micropipette. $3 \times 10^5$ cells in a total volume of 50 μl were used for the injection. The cells were mixed with Trypan blue prior to the injection. The recipient mice were anesthetized with 0.017 mL/g body wt. Avertin. An incision was made across the lower abdominal wall and the testis was gently pulled to the exterior through the incision by pulling on the fat pad associated with the testis. The vas efferens was exposed and approximately 20 μL of cell suspension was injected into the vas efferens using a glass micropipette held in a steel micropipette holder (Leitz). The cells were expelled from the pipette using air pressure from a 20 mL glass syringe. Prior to the transfer of transfected germ cells to the recipient animals, the recipient testes were depopulated of endogenous male germ cells.

Example 13
Depopulating the Recipient Testis of Male Germ Cells.

Comparison of Depopulating Treatments. Eight-week-old C57BL/6J mice were allowed to acclimatize for a few days and then were assigned to one of the following three treatment groups. They received: (1) 400 Rad gamma irradiation; (2) 4 μG/g body weight of busulfan (1,4-butanediol dimethanesulphonate; Mylleran, Glaxo Wellcome); or (3) a combination treatment of busulfan (4 μg/g body wt) followed one week later by 400 Rad of gamma irradiation ("busulfan/400 Rad" treatment). A fourth group of untreated C57BL/6J mice of the same age as the treatment groups was used as a control. There were 24 mice in each treatment group, and 3 mice were mice sacrificed at each of the following time intervals after treatment: 5 hours, 24 hours, 48 hours, 72 hours, 1 week, 2 weeks, 1 month and 2 months after treatment.

In addition, other C57BL/6J mice receiving the combined busulfan/400 Rad treatment were examined histologically at time points up to five months after treatment (the testes of these other mice were fixed overnight in 4% paraformaldehyde in PBS, pH 7.4 at 4° C., before sectioning and H&E staining).

Delivery of an Alkylatini Agent to Recipient Vertebrates. The male mice receiving busulfan received a dose of 4 μg busulfan per g body wt. The busulfan was first dissolved 8 mg/mL in 100% dimethyl sulfoxide (DMSO) then, immediately before injection, was diluted 1:1 in phosphate buffered saline, pH 7.4. The mice were injected with the diluted busulfan solution intraperitoneally.

Irradiation Treatment of Recipient Vertebrates. For the gamma irradiation treatment, mice were anesthetized with 0.017 mL/g body wt. of 2.5% Avertin. Gamma irradiation was specifically directed to the testis in the following manner. Each mouse was placed in a lead chamber with only the testis and lower abdomen exposed through elliptical holes to the irradiating source ($^{137}$Cs Gammacell 40 irradiator [Nordion]). There were six aligned holes in the floor and roof of the chamber through which the gamma radiation passed unobstructed. After irradiation the animals were allowed to recover from the anesthesia on a warm heating pad or water bed until they regained consciousness.

Histology. At selected time points, mice from each treatment group were euthanized, and testicular tissues to be examined were fixed in 10% formalin in PBS, pH 7.4, at 4° C. for 24 hours. Small slits in the testis capsule were made to allow penetration of the fixative. Fixed samples were washed four times with PBS, and embedded in paraffin using a Tissue Tek-II tissue processor (MET). Sections of 8 μm thickness were cut, stained with haemotoxylin and eosin (H&E), and mounted with Aquamount (Lerner Laboratories) on glass slides with coverslips. The sections were viewed on a Zeiss or Olympic light microscope with a 40× objective lens (total magnification 400×).

Quantitative Histologic Analysis. Quantitative data were collected from the testes of two animals for each of the treatment groups at two months after treatment. (Table 1). For the control group only one mouse was used. The seminiferous tubules in a single section were counted using a 5× objective on a Zeiss light microscope (50× total magnification). Individual seminiferous tubules were examined at 400× total magnification. Seminiferous tubules were considered severely damaged if hardly any cells remained in the tubule, and the tubule consisted of a basement membrane with a single layer of cells, mostly spermatogonia, lying along the basement membrane. Moderately damaged tubules were tubules, in which some of the spermatogenic layers close to the lumen were partially sloughed off. Spermatozoan heads were counted in the tubules and averaged over the total number of tubules counted.

Results of Histological Analysis. Obvious histological changes were not seen in the testis until two weeks after treatment. (Data no shown). FIG. 1 shows a histologic time course of mouse testis that has been treated with a combination of the alkylating agent busulfan and gamma irradiation as described above.

FIG. 1A shows a 400× cross section through several seminiferous tubules from a mouse two weeks after busulfan/400 Rad treatment. In FIG. 1A, spermatogenesis has been severely disrupted, all the mature spermatozoa have been lost and no spermatids or spermatocytes are present. A few Sertoli cell nuclei and spermatogonia can be seen in the periphery along the basement membrane.

Figure 1B:
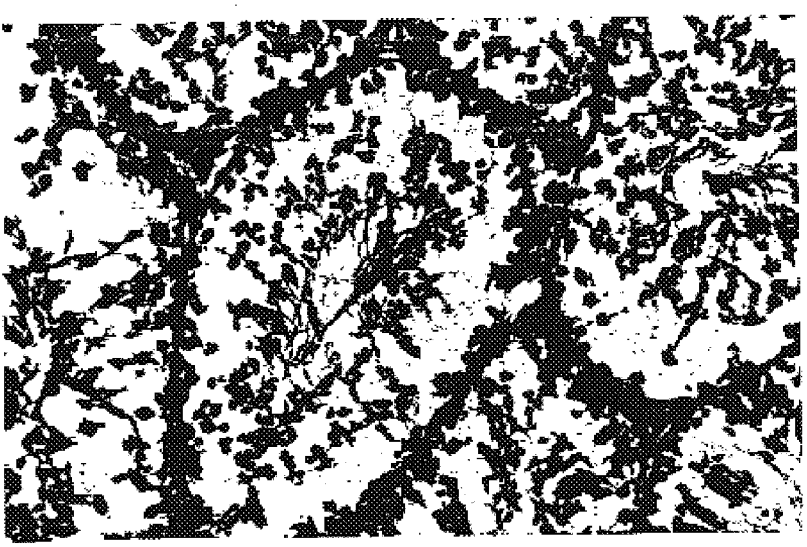
FIG. 1B shows several sectioned seminiferous tubules from a mouse 6 weeks after busulfan/400 Rad treatment.

FIG. 1B shows a 400× cross section through several seminiferous tubules from a mouse 6 weeks after busulfan/400 Rad treatment. In FIG. 1B, there is evidence of the re-establishment of spermatogenesis. Some spermatids and spermatozoa are seen as well as a few spermatocytes.

Figure 1C:
FIG. 1C shows several sectioned seminiferous tubules from a mouse 5 months after busulfan/400 Rad treatment.

By about 3 months most of the seminiferous tubules had at least partially recovered and all stages of spermatogenesis appear to be represented. (Data not shown). FIG. 1C shows a 400× cross section through several seminiferous tubules from a mouse 5 months after busulfan/400 Rad treatment. Spermatogenesis had returned to normal at this stage.

Figure 2A:
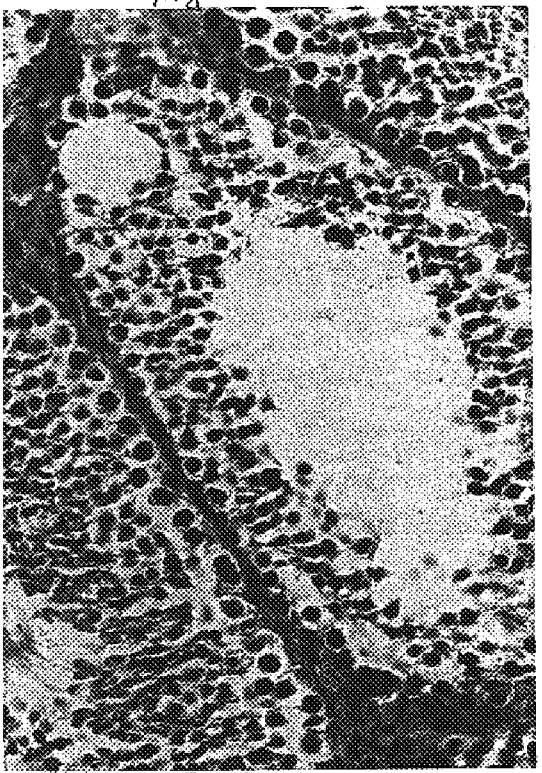
FIG. 2A shows a section of testicular tissue after treatment with busulfan (4 mg/kg).
Figure 2D:
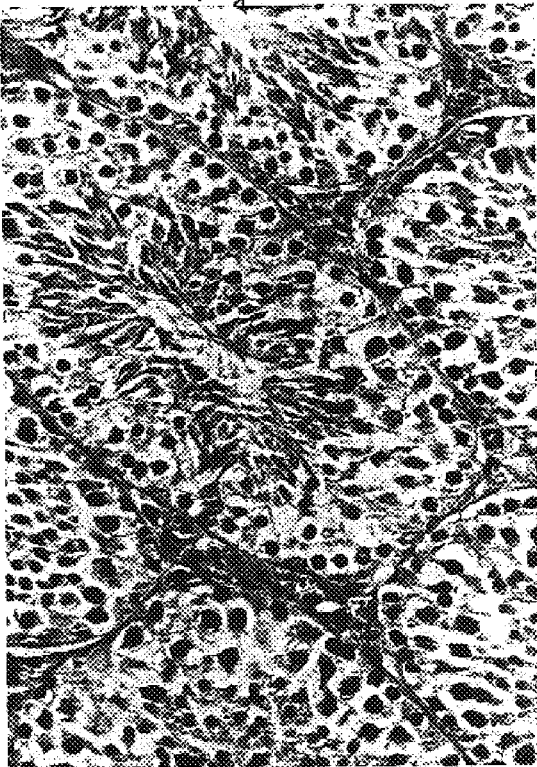
FIG. 2D shows a section of testicular tissue from an untreated control C57BL/6J mouse after 2 months from the start of the experiment.
Figure 2B:
FIG. 2B shows a section of testicular tissue after combined busulfan/400 Rad treatment.
Figure 2C:
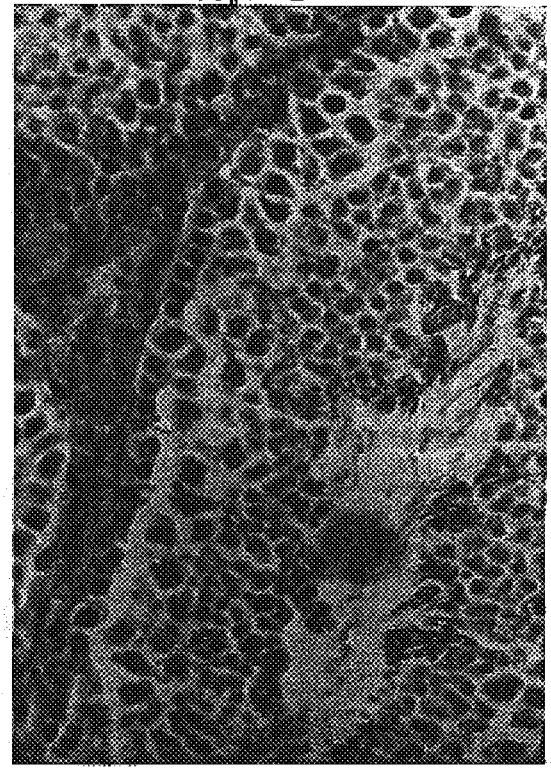
FIG. 2C shows a section of testicular tissue after treatment with 400 Rad gamma irradiation.

The three treatment groups described above were also compared. The most dramatic differences among the groups were seen at two months after treatment. At two months the mice that were treated with the combined busulfan/400 Rad gamma irradiation treatment showed the greatest number of substantially depopulated seminiferous tubules. (FIG. 2B). Seminiferous tubules from this group also contained a smaller average number of sperm heads per seminiferous tubule and the greatest proportion of severely and moderately damaged seminiferous tubules compared to the other treatment groups and the control mice. (Table 1). Treatment of the mice with either 400 Rad gamma irradiation or busulfan alone also resulted in damage to the spermatogenic process, including sloughing of cells into the lumen of the tubule, and substantially fewer mature spermatozoan heads compared to the controls, but to a significantly lesser extent than exemplified by the busulfan/400 Rad treatment group.

These results clearly demonstrate that a combination of treatment with an alkylating agent and gamma irradiation is a more effective method of depopulating a vertebrate testis of male germ cells than either of the two treatments alone.

TABLE 2

Comparison of Various Methods of Depopulating a Vertebrate Testis of Male Germ Cells.

| Treatment | No. Tubules Counted | No. Severely damaged | No. Moderately damaged | Total No. Sperm heads | Average No. sperm heads/tubule |
|---|---|---|---|---|---|
| Control | 50 | 0 | 0 | 1733 in 50 tubules | 35 |
| Busulfan/400R | 50 | 15(30%) | 3(6%) | 460 in 50 tubules | 9 |
| Busulfan/400R | 57 | 14(24%) | 8(14%) | 383 in 50 tubules | 8 |
| Busulfan | 70 | 1(1%) | 5(7%) | 957 in 50 tubules | 19 |
| Busulfan | 69 | 3(10%) | 2(3%) | 764 in 50 tubules | 15 |
| 400R | 52 | 2(4%) | 1(2%) | 1005 in 50 tubules | 20 |
| 400R | 41 | 2(5%) | 3(7%) | 827 in 41 tubules | 20 |

Example 14

In vivo Transduction Using a Lentiviral Vector

A lentiviral vector was used to transduce (genetically alter or modify) a male germ cells of mice in vivo. Specifically, a pseudo-typed HIV-derived lentiviral vector (L. Naldini et al., *In vivo gene delivery and stable transduction of nondividing cells by a Lentiviral vector*, Science 272:263–67 [1996]), was used, as modified by Carlos Lois to express Green Flourescent Protein (GFP) under the transcriptional control of the CMV promoter instead of the LacZ promoter (HR'GFP).

Recipient C57BL/6J mice were treated with busulfan 44 days prior to viral infection. C57BL/6J male mice were injected intraperitoneally with 0.1 ml busulfan at a concentration of 2 mg/ml. The dose was 4 $\mu$g busulfan/gm body wt. One pretreated mouse was anesthetized with Avertin (0.017 mls/gm body wt.), and a ventral midline incision was made and the right testis exposed.

The vas efferentia were dissected away from the fat, and ten microlitres of HIV-derived GFP vector, HR'GFP, at a titer of $1 \times 10^9$ particles/ml were injected into the seminiferous tubules of the right testis via the vas efferens of a busulfan-treated C57BL/6J mouse. Injection was done with a quartz glass micropipette attached to a Picospritzer II. The Picospritzer was set at 80 psi and gave 1 second bursts upon manual depression of a foot pedal. All the seminiferous tubules of the testis can be reached with a single injection as the vas efferens leads to a common chamber, the rete testis, from which all the tubules radiate. The left testis was not injected and was used as a control. Transduction of the testicular cells within the tubules was widespread.

Twenty one days after infection, the mouse was sacrificed and the testes were fixed overnight in 4% paraformaldehyde in PBS, pH 7.4 at 4° C. The testes were washed three times in PBS and placed in 20% sucrose overnight at 4° C. The testes were frozen in OCT and sectioned at 8 $\mu$m on a cryostat. The sections were thawed to room temperature immersed in phosphate saline buffer and viewed on a Zeiss 310 confocal microscope. The laser was set at a wavelength of 488 nm.

Figure 3A:
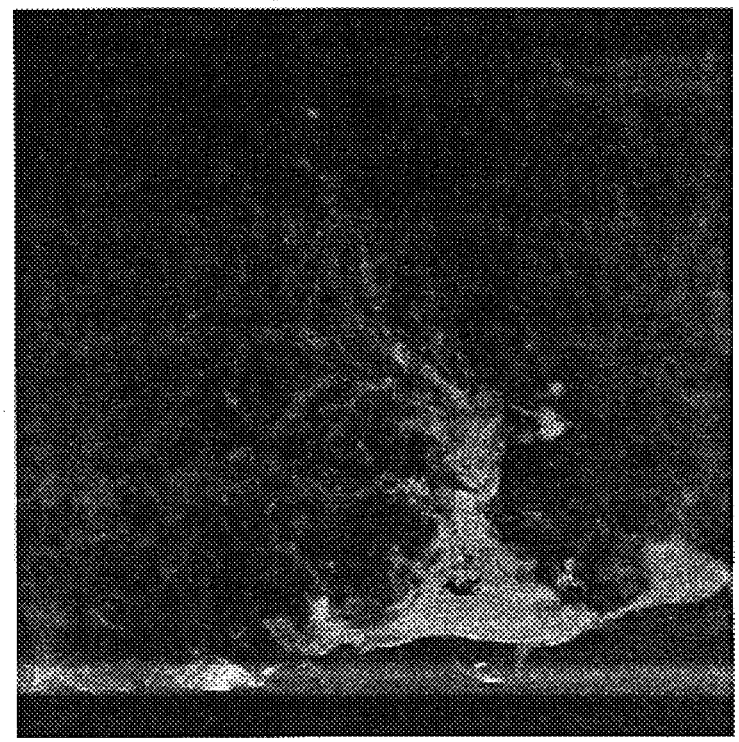
FIG. 3A shows a transduced Sertoli cell and is the maximum intensity projection of 19 images.
Figure 3B:
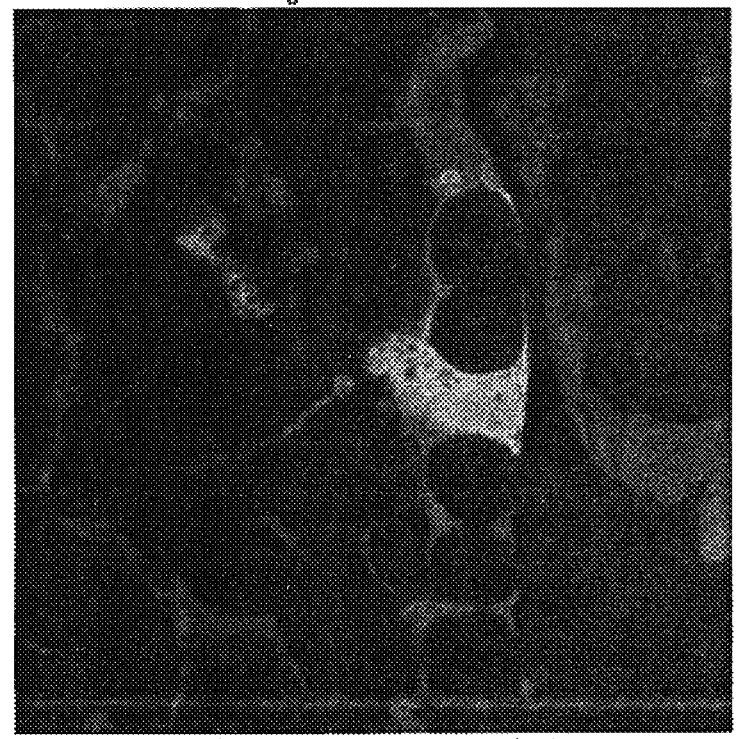
FIG. 3B shows genetically altered (transduced) spermatogonia along the basement membrane of the seminiferous tubule.

Green fluorescence was seen in all the seminiferous tubules that were viewed, although the intensity was greatest in the tubules at the surface of the testis. Transduction was seen in the Sertoli support cells (FIG. 3A) as well as in the spermatogonia along the basement membrane (FIG. 3B), but little was seen in the spermatocytes or spermatids. Very few mature spermatozoa were present due to the Busulfan treatment. No fluorescence was seen in the left testes used as control. This shows that male germ cells can be transduced by a lentiviral-derived vector.

The foregoing examples being illustrative but not an exhaustive description of the embodiments of the present invention, the following claims are presented.

What is claimed:

1. A method of transferring male germ cells genetically altered with at least one polynucleotide encoding a gene product to a substantially depopulated testis of a recipient male non-human mammal, comprising:

administering by injection into a gonad of a donor male non-human mammal a gene delivery mixture comprising at least one retroviral gene delivery agent that comprises at least one polynucleotide encoding a gene product in operable linkage with a promoter, and at least one polynucleotide encoding a genetic selection marker in operable linkage with a promoter that is active in a male germ cell, wherein said gonad contains germ cells of the donor male non-human mammal, and wherein said germ cells are selected from the group consisting of spermatogonial stem cells, type B spermatogonia, primary spermatocytes, preleptotene spermatocytes, leptotene spermatocytes, zygotene spermatocytes, pachytene spermatocytes, secondary spermatocytes, spermnatids, and spermatozoa;

allowing the at least one polynucleotide encoding a gene product and the at least one polynucleotide encoding a genetic selection marker to be taken up by, and released into, at least one of the germ cells of the donor male non-human mammal, so that the released polynucleotides are incorporated into the genome of the at least one of the germ cells;

isolating or selecting from the donor male non-human mammal at least one genetically altered germ cell carrying the at least one polynucleotide encoding a gene product, and expressing the at least one polynucleotide encoding a genetic selection marker, administering the at least one genetically altered germ cell, thus isolated or selected, to at least one testis of a recipient male non-human mammal of the same species as the donor male non-human mammal, said recipient male non-human mammal having at least one testis substantially depopulated of male germ cells by administration to said recipient male non-human mammal of a dose of an alkylating agent combined with a dose of gamma radiation prior to the administration of the genetically altered germn cells from the donor male non-human mammal; and allowing the administered germ cells to lodge in a seminiferous tubule of the recipient male non-human mammal.

2. The method of claim 1, wherein gene delivery is conducted under conditions of temperature of about 25° C. to about 38° C.

3. The method of claim 1, wherein the viral vector is a lentiviral vector.

4. The method of claim 3, wherein the lentiviral vector is a human immunodeficiency virus vector.

5. The method of claim 1, wherein the viral vector is a Moloney murine leukemia virus-derived vector.

6. The method of claim 1, wherein the promoter in operable linkage with the polynucleotide encoding a gene product and/or with the polynucleotide encoding a genetic selection marker is selected from the group consisting of a cyclin A1 promoter, a c-kit promoter, a B-Myb promoter, a c-raf-1 promoter, an ATM (ataxia-telangiectasia) promoter, a RBM (ribosome binding motif) promoter, a DAZ (deleted in azoospermia) promoter, a XRCC-1 promoter, a HSP 90 (heat shock gene) promoter, and a FRMI (from fragile X site) promoter.

7. The method of claim 1, wherein the promoter in operable linkage with the polynucleotide encoding a gene product and the promoter in operable linkage with the polynucleotide encoding a genetic selection marker are the same promoter.

8. The method of claim 1, wherein the mammal is a non-human primate, a farm mammal, or a marine mammal.

9. The method of claim 1, wherein the polynucleotide encoding a gene product is derived from the same species of non-human mammal as the recipient non-human mammal.

10. The method of claim 1, wherein the polynucleotide encoding a gene product is derived from a human.

11. The method of claim 1, wherein the non-human mammal is selected from the group consisting of wild non-human mammals and domesticated non-human mammals.

12. The method of claim 1, wherein the polynucleotide encoding a gene product is derived from a mammal-selected from the group consisting of human and non-human primates, canines, mice, rats, gerbils, hamsters, rabbits, felines, swine, pachyderms, marine mammals, equines, ovines and bovines.

13. The method of claim 1, wherein the alkylating agent is busulfan, chlorambucil, cyclophosphamide, melphalan, or ethyl ethanesulfonic acid.

14. The method of claim 1, wherein the dose of the alkylating agent is about 4 to 10 mg per kg of body weight.

15. The method of claim 1, wherein the dose of gamma radiation is specifically directed to a testis of said recipient male non-human mammal and the dose of gamma radiation is about 200 to 800 Rads.

16. The method of claim 15, wherein the dose of gamma radiation is about 350 to 450 Rads.

17. The method of claim 1, wherein Leydig and/or Sertoli cells are co-administered to the testis of the recipient male non-human mammal along with the isolated or selected germ cells.

18. The method of claim 1, wherein the genetic selection marker is a fluorescent protein or light-emitting protein.

19. The method of claim 18, wherein the fluorescent or light-emitting protein is a green fluorescent protein, yellow fluorescent protein, blue fluorescent protein, phycobiliprotein, luciferase, or apoaequorin.

20. An in vivo method of incorporating a polynucleotide into germ cells of a male non-human mammal for the production of transgenic non-human mammals, comprising:

administering by injection into a testis of a male non-human mammal a gene delivery mixture comprising at least one retroviral gene delivery agent, and at least one polynucleotide encoding a gene product in operable linkage with a promoter, wherein said testis contains germ cells of the male non-human mammal and wherein said germ cells are selected from the group consisting of spermatogonial stem cells, type B spermatogonia, primary spermatocytes, preleptotene spermatocytes, leptotene spermatocytes, zygotene spermatocytes, pachytene spermatocytes, secondary spermatocytes, spermatids, and spermatozoa;

allowing the at least one polynucleotide encoding a gene product to be taken up by, and released into, at least one of the germ cells of the male non-human mammal, so that the released polynucleotides are incorporated into the genome of the at least one of the germ cells of said non-human mammal, thereby producing a transgenic non-human mammal.

21. The method of claim 20, wherein the gene delivery agent further comprises a c-kit ligand.

22. The method of claim 20, wherein the gene delivery mixture further comprises an immunosuppressing agent.

23. The method of claim 22, wherein the immunosuppressing agent is selected from the group consisting of cyclosporin and corticosteroids.

24. The method of claim 20, where the injection of the gene delivery mixture is a percutaneous injection.

25. The method of claim 20, wherein the injection of the gene delivery mixture is into the vas efferens of the testis.

26. The method of claim 20, wherein the injection of the gene delivery mixture is into the seminiferous tubule of the testis.

27. The method of claim 26, wherein the injection of the gene delivery mixture is into the rete of the testis.

28. The method of claim 20, wherein the non-human mammal is selected from the group consisting of non-human primates, canines, mice, rats, gerbils, hamsters, rabbits, felines, swine, pachyderms, marine mammals, equines, ovines and bovines.

29. The method of claim 20, wherein the male non-human mammal is selected from the group consisting of wild non-human mammals and domesticated non-human mammals.

30. The method of claim 20, wherein the polynucleotide encoding a gene product is derived from a different species from the male non-human mammal.

31. A method of isolating or selecting a male germ cell transfected with at least one polynucleotide encoding a gene product and at least one polynucleotide encoding a genetic selection marker, comprising:

performing the method of claim 20, wherein the gene delivery mixture further comprises at least one polynucleotide encoding a genetic selection marker; and isolating or selecting a genetically altered male germ cell by detection of the genetic selection marker.

32. The method of claim 31, wherein the genetic selection marker is a fluorescent protein or light-emitting protein.

33. The method of claim 32, wherein the fluorescent or light-emitting protein is a green fluorescent protein, yellow fluorescent protein, blue fluorescent protein, phycobiliprotein, luciferase, or apoaequorin.

34. An in vivo method of incorporating a polynucleotide into germ cells of a male non-human mammal, comprising:

administering by injection into a testis of a male non-human mammal a gene delivery mixture comprising at least one lentiviral-derived gene delivery agent, and at least one polynucleotide encoding a gene product in operable linkage with a promoter, wherein said testis contains germ cells of the male non-human mammal, and wherein said germ cells are selected from the group consisting of spermatogonial stem cells, type B spermatogonia, primary spermatocytes, preleptotene spermatocytes, leptotene spermatocytes, zygotene spermnatocytes, pachytene spermatocytes, secondary spermatocytes, spermatids, and spermatozoa;

allowing the at least one polynucleotide encoding a gene product to be taken up by, and released into, at least one of the germ cells of the male non-human mammal, so that the released polynucleotides are incorporated into the genome of the at least one of the germ cells of said non-human mammal.

35. The method of claim 20, wherein the gene delivery mixture further comprises polybrene.

36. The method of claim 34, wherein the gene delivery agent further comprises a c-kit ligand.

37. The method of claim 34, wherein the gene delivery mixture further comprises an immunosuppressing agent.

38. The method of claim 37, wherein the immnunosuppressing agent is selected from the group consisting of cyclosporin and corticosteroids.

39. The method of claim 34, where the injection of the gene delivery mixture is a percutaneous injection.

40. The method of claim 34, wherein the injection of the gene delivery mixture is into the vas efferens of the testis.

41. The method of claim 34, wherein the injection of the gene delivery mixture is into the seminiferous tubule of the testis.

42. The method of claim 34, wherein the injection of the gene delivery mixture is into the rete of the testis.

43. The method of claim 34, wherein the non-human mammal is selected from the group consisting of non-human primates, canines, mice, rats, gerbils, hamsters, rabbits, felines, swine, pachyderms, marine mammals, equines, ovines and bovines.

44. The method of claim 34, wherein the male non-human mammal is selected from the group consisting of wild non-human mammals and domesticated non-human mammals.

45. The method of claim 34, wherein the polynucleotide encoding a gene product is derived from a different species from the male non-human mammal.

* * * * *

UNITED STATES PATENT AND TRADEMARK OFFICE
CERTIFICATE OF CORRECTION

PATENT NO. : 6,734,338 B1
DATED : May 11, 2004
INVENTOR(S) : Carol W. Readhead and Robert Winston It is certified that error appears in the above-identified patent and that said Letters Patent is hereby corrected as shown below:

Column 1,
Line 25, insert -- . -- after "gene therapy".
Line 39, insert -- . -- after "function".
Line 40, insert -- . -- after "diseases".
Line 47, insert -- . -- after "transplantation:.

Column 2,
Line 43, delete "el al." and insert -- et al. --.

Column 3,
Line 28, delete "oftestis" and insert -- of testis --.

Column 4,
Line 1, delete "spermatogenesi" and insert -- spermatogenesis --.
Line 5, delete "cryptochidism" and insert -- cryptorchidism --.
Line 16, delete "busutfan" and insert -- busulfan --.

Column 8,
Line 58, delete "restablish" and insert -- re-establish --.
Line 60, delete "testes" and insert -- testis --.
Line 64, delete ".".

Column 10,
Line 18, insert -- . -- after "thereof"
Line 52, delete "is" and insert -- are --.
Line 59, delete "a".

Column 13,
Line 63, insert -- as -- before "rhinoceros".

Column 15,
Line 3, delete "desired" and insert -- desire --.
Line 53, insert -- more -- before "mutations".

Column 16,
Line 50, delete "polvlysine" and insert -- polylysine --.

UNITED STATES PATENT AND TRADEMARK OFFICE
CERTIFICATE OF CORRECTION

PATENT NO. : 6,734,338 B1
DATED : May 11, 2004
INVENTOR(S) : Carol W. Readhead and Robert Winston It is certified that error appears in the above-identified patent and that said Letters Patent is hereby corrected as shown below:

Column 17,
Line 4, delete "carboduimide" and insert -- carbodiimide --.

Column 20,
Line 14, delete "0" and insert -- O --.
Line 21, delete "Nomaski" and insert -- Nomarski --.

Column 21,
Line 42, delete "alkylatin" and insert -- alkylating --.

Column 22,
Line 26, delete "no" and insert -- not --.

Column 24,
Line 35, delete "spermnatids" and insert -- spermatids --.

Column 25,
Line 32, delete "mammal-selected" and insert -- mammal selected --.

Column 27,
Line 1, delete "spermnatocytes" and insert -- spermatocytes --.
Line 27, delete "method of claim 26" and insert -- method of claim 20 --.

Signed and Sealed this

Twenty-second Day of March, 2005

JON W. DUDAS
*Director of the United States Patent and Trademark Office*